(12) United States Patent
Danthinne

(10) Patent No.: US 8,709,778 B2
(45) Date of Patent: Apr. 29, 2014

(54) METHOD OF ADENOVIRAL VECTOR SYNTHESIS

(75) Inventor: Xavier Danthinne, Boise, ID (US)

(73) Assignee: Xavier Danthinne, Boise, ID (US)

(*) Notice: Subject to any disclaimer, the term of this patent is extended or adjusted under 35 U.S.C. 154(b) by 1057 days.

(21) Appl. No.: 12/260,069

(22) Filed: Oct. 28, 2008

(65) Prior Publication Data
US 2010/0105110 A1    Apr. 29, 2010

(51) Int. Cl.
*C12N 7/00* (2006.01)
*C12Q 1/00* (2006.01)
*C12Q 1/70* (2006.01)
*C12Q 1/68* (2006.01)
*C12P 21/06* (2006.01)
*A61K 39/12* (2006.01)
*A61K 39/23* (2006.01)

(52) U.S. Cl.
USPC ............. 435/235.1; 424/233.1; 424/199.1; 435/4; 435/5; 435/6.1; 435/69.1

(58) Field of Classification Search
None
See application file for complete search history.

(56) References Cited

U.S. PATENT DOCUMENTS

| 5,981,225 | A * | 11/1999 | Kochanek et al. | ........... 435/69.1 |
| 6,291,243 | B1 | 9/2001 | Fogarty | |
| 6,793,926 | B1 | 9/2004 | Rasty | |
| 2002/0136708 | A1 * | 9/2002 | Graham et al. | ........... 424/93.21 |
| 2005/0123898 | A1 | 6/2005 | Hillgenberg | |
| 2005/0287120 | A1 | 12/2005 | Fisher | |
| 2007/0178115 | A1 | 8/2007 | Tang | |

OTHER PUBLICATIONS

Kochanek et al., A new adenoviral vector: Replacement of all viral coding sequences with 28 kb of DNA independently expressing both full-length dystrophin and 8-galactosidase, 1996, PNAS, vol. 93, pp. 5731-5736.*
International Search Report for PCT/US2008/087885.
Hartigan-O'Conner, D., et al., J. Virol. 1999. 73:7835-7841.
Hartigan-O'conner, D., et al., Hum. Gene Ther. 2002. 13:519-531.
Miyake, S., et al., Proc. Natl. Acad. Sci. USA. 1996. 93:1320-1324.

* cited by examiner

*Primary Examiner* — Benjamin P Blumel

(57) ABSTRACT

This invention provides methods for adenoviral vector synthesis. The present invention further provides methods for binding adenovirus terminal protein obtained from virus to linear DNA. The present invention further provides a recombinant adenovirus from which the adenovirus terminal protein can be purified with an inverted terminal repeat DNA sequence.

17 Claims, 12 Drawing Sheets

METHOD OF ADENOVIRAL VECTOR SYNTHESIS

This invention was made with government support under Grant 5R44GM062043 awarded by the National Institutes of Health. The government has certain rights in the invention.

FIELD OF THE INVENTION

The present disclosure relates to methods for adenoviral vectors synthesis. The present disclosure further relates to methods for binding adenovirus terminal protein obtained from virus to linear DNA.

BACKGROUND

Adenoviruses

Adenoviruses are nonenveloped icosahedral viruses containing double stranded DNA (dsDNA). Adenoviruses are stable to chemical or physical agents and adverse pH conditions, allowing for prolonged survival. In humans there are over 51 different serotypes. The adenovirus genome is linear, non-segmented dsDNA of approximately 30-38 kilobases in size. The virus is reliant on the host cell for survival and replication. The genome has a terminal 55 kilodalton (kDa) protein associated with each of the 5' ends of the linear dsDNA. These proteins are used as primers in viral replication and ensure that the ends of the virus linear genome are adequately replicated.

Adenoviral Vectors and Gene Transfer

Adenovirus has become a tool to transfer genes into mammalian cells. Adenoviral vectors have numerous advantages compared to other viral vectors (Roberts, P., et al., *Trends in Biotechnol.* 1998. 16:35-40): they are rapidly manipulated in vitro, have a moderately high cloning capacity, and can be grown to extremely high titers (Lieber. A., et al., *J. Virol.* 1999. 73:7835-7841; Hartigan-O'Connor, D., et al., *Methods in Enzymol.* 2002. 346:224-246). Adenoviruses are currently used in about one fourth of gene therapy clinical trials. Since the early 1990s, the number of publications related to adenoviral vectors has increased exponentially. This number is expected to increase even further, as dozens of new genes are being discovered daily (through the sequencing of genomes), and techniques, such as microarrays are available to screen thousands of genes in a short period of time. Gene transfer techniques, such as adenovirus will be increasingly utilized. Research of adenoviral vectors continues as the requirement for larger cloning capacities increases. However, at least two important disadvantages undermine the use of adenoviral vectors: their construction is a time-consuming process, and adenoviral vectors elicit a strong immune response at high doses in vivo.

Methods for the Construction of Adenoviral Vectors

First-Generation Adenoviral Vectors

First-generation adenoviral vectors are adenoviruses in which an exogenous DNA replaces the E1 region, or in some cases the E3 region of the viral genome.

Several techniques have been developed which facilitate the construction of first-generation adenoviral vectors. They can be classified into three categories.

The first category includes methods based on a homologous recombination between a plasmid carrying the gene of interest, and a viral DNA (Kozarsky, K. and Wilson, J., *Curr. Op. Genet. Dev.* 1993. 3:499-503; Imler, J., et al., *Gene Ther.* 1995. 2:263-268). Viral plaques appear on average 10 to 15 days after transfection since this recombination is an inefficient process. Moreover, because the viral DNA is extracted from virions, contamination of the virus preparation is frequent, and time-consuming virus purification by plaque assays must be performed. This entire procedure takes 2 to 3 months.

A second category of methods eliminates these problems by using infectious circular adenoviral DNAs that can replicate in bacteria as plasmids (Bett, A., et al., *Proc. Natl. Acad. Sci. USA.* 1994. 91:8802-8806). No viral background is obtained since these DNAs are too large to be packaged into viral particles. However, the method still requires a homologous recombination event, which is inefficient, and these circular DNAs are replicated less efficiently than linear viral DNAs. Moreover, these plasmids are unstable in *E. coli*, and their manipulation is therefore difficult, due to the presence of a 200 base pair long palindrome resulting from the head-to-head joining of both ITRs.

A third category includes methods that reconstitute in a plasmid the entire sequence of the desired recombinant virus (He, T., et al., *Proc. Natl. Acad. Sci. USA.* 1998. 95:2509-2514; Mizuguchi, H. and Kay, M. *Hum. Gene Ther.* 1998. 9:2577-2583; Danthinne, X., et al., *Gene Ther.* 2000. 7(1):80-87). Although their construction has been simplified, these plasmid DNAs are poorly infectious: viral plaques take on average 7 to 10 days to appear, and in some instances require 2 to 3 weeks. Given the fact that the life cycle of a virus is about 24 hours, the generation of virus from plasmid DNA is very slow.

Second-Generation and Other Mutant Adenoviral Vectors

Second-generation adenoviral vectors are first-generation vectors deleted for additional genes involved in viral replication (such as, for example, the E2a, E2b or E4 regions) (Amalfitano, A., *J. Virol.* 1998. 72:926-933; Gorziglia, M., et al., *Virol.* 1999. 73:6048-6055). Although no method has been designed specifically for their construction, the same discussion as for the first-generation adenoviral vectors applies: plasmid-based methods are a preferred choice since they eliminate potential viral contaminations, but they suffer from the poor infectivity of the viral DNAs isolated from plasmids.

Plasmid-based approaches are also used to construct other mutant adenoviruses; for example, viruses targeted to specific cell types by substituting heterologous ligands for the fiber knob (Einfeld, D., et al., *Proc. Natl. Acad. Sci. USA.* 1996. 93:5731-5736). The recovery of such mutant viruses would be difficult, not only because of the low efficiency of recovering virus from bacterial plasmids, but also because the targeted membrane receptor might not be as efficient for virus attachment and internalization as the natural receptor, and altering the fiber may affect virion assembly and stability.

Gutless Adenoviral Vectors

Gutless adenoviral vectors are also referred to as "helper-dependent," "gutted," or "high-capacity" adenoviral vectors. They are deleted for the entirety of the viral genome, except for the sequences necessary for replication and packaging. These vectors have two important advantages: first, they can accommodate up to 36 kilobases of exogenous DNA; and second, they are unable to express viral genes and therefore, they should elicit a decreased immune response and a sustained gene expression (Hartigan-O'Connor, D., et al., *J. Virol.* 1999. 73:7835-7841; Kochanek, S., et al., *Proc. Natl. Acad. Sci. USA.* 1996. 93:5731-5736; Parks, R., et al., *Proc. Natl. Acad. Sci. USA.* 1996. 93:13565-13570).

The starting point for the production of a gutless virus is a plasmid DNA that contains the viral ITR's, the packaging signal, and the exogenous DNA. This plasmid generally is linearized and transfected into a cell line with a helper DNA, which provides in trans all the viral products necessary for virus replication. Replication of the helper virus eventually causes lysis of the cells. Unfortunately, the titer of gutless virions is very small compared to the titer of helper virus. Titers of less than 100 particles per milliliter are often obtained on the first passage (Hartigan-O'Connor, D., et al., *J. Virol.* 1999. 73:7835-7841). To increase the proportion of gutless viruses, the initial lysate must be serially passaged (up to five times), which is very time-consuming. Finally, both gutless and helper viruses must be separated on the basis of their different density on a cesium chloride gradient.

In summary, methods that produce first- and second-generation adenoviral vectors, mutant adenoviruses and gutless viruses, preferentially use bacterial plasmids to generate the recombinant virus. Once transfected into helper cells, these plasmids unfortunately are inefficient in generating the virus; typically, it takes 7 to 10 days and sometimes several weeks to generate viral plaques, or the viral titer is very low (gutless viruses).

Without being limited by theory, the presence of additional nucleotides at the ends of the viral DNA, originating from the restriction site used for linearization of the plasmid, and the absence of the terminal protein, may prevent efficient initiation of DNA replication and may contribute to the low infectivity of these DNAs.

Adenoviral Terminal Protein (TP)

In a virion, the viral DNA is covalently linked to the 55 kDa terminal protein (TP). Genome-linked TP has at least three roles during infection. First, TP determines the sub-nuclear location of viral DNA templates for transcription and replication by binding strongly to the nuclear matrix (Shaack, J., et al., *Genes Dev.* 1990. 4:1197-1208). Second, TP directly influences DNA replication by altering the structure of linked origin of DNA replication and stabilizing the binding of a pre-terminal protein-viral DNA polymerase complex to its binding site in the viral origin of DNA replication (Pronk, R. and van der Vliet, P. *Nucl. Acids Res.* 1993. 21:2293-2300). Third, TP may protect the viral DNA against cellular exonucleases (Hay, R., et al., in: *Molecular repertoire of adenoviruses II* (eds W. Doerfler and P. Bohm), 31-48 (1996)).

The presence of TP at both ends of the viral genome increases its infectivity by two to three orders of magnitude, compared to protease-treated DNA ((van Bergen, B., et al., *Nucl. Acids Res.* 1983. 11:1975-1988; Pronk, R. and van der Vliet, P. *Nucl. Acids Res.* 1993. 21:2293-2300; Sharp, P., et al., *J. Virology.* 1976. 75:442-456; Jones, N. and Shenk, T. *Cell.* 1978. 13:181-88). Plasmid DNAs are obviously not linked to the adenoviral TP, and in addition, both origins of replication contain a few additional nucleotides originating from the restriction site used to linearize the plasmid. Without being limited by theory, these facts may explain the low infectivity of plasmid DNAs.

Methods for Constructing Adenoviruses using the Terminal Protein

A method designed to construct first-generation adenoviruses with the help of the adenoviral terminal protein, uses a DNA-terminal protein complex purified from virions (Miyake, S., et al., *Proc. Natl. Acad. Sci. USA.* 1996. 93:1320-1324). This viral DNA is digested extensively using a specific restriction enzyme, and transfected with a plasmid DNA containing the gene of interest into helper cells. This technique allows recovery of hundreds of plaques. However, it still requires the very inefficient homologous recombination event in helper cells and 30% of the plaques are negative. The very time-consuming process of screening for the recombinant virus is therefore still required.

In another approach, a stable cell line was generated that expresses both the adenoviral DNA polymerase and the pre-terminal protein (Hartigan-O'Connor, D., et al., *J. Virol.* 1999. 73:7835-7841). This cell line was shown to increase the efficiency of generation of recombinant viruses from plasmids. Unfortunately, because it is derived from the "293" cell line, it cannot prevent the formation of replication-competent adenoviruses (RCA) from first-generation adenoviral vectors. Therefore, time-consuming virus purification and tests for the presence of RCAs must be performed if the virus is used in clinical trials. Moreover, cells lines expressing the terminal protein are difficult to establish and to maintain because of the toxicity of the terminal protein. This complicates the construction of helper cell lines that express additional heterologous genes, coding for instance for a membrane receptor to which a recombinant virus is targeted.

In another approach, gutted Ad vectors from plasmid-derived substrates or from synthetic TP-linked substrates made in vitro have been attempted (Hartigan-O'Connor, D., et al., *Hum. Gene Ther.* 2002. 13:519-531). Efficient rescue required cotransfection of gutted and helper genomes with identical origins of replication. Cotransfection of plasmid-derived substrates was 30 times more efficient than transfection/infection. Linkage of gutted vector genomes to TP and expression of Cre recombinase further increased rescue efficiency.

Gutless adenovirus vectors constitute a promising tool for gene transfer because of their unique transgene capacity (up to 36 kb), prolonged persistence and their reduced cytotoxicity and immunogenicity compared to first-generation vectors. One of the major hurdles in gutless adenovirus vectors production is the difficulty in large-scale production; a difficulty that has contributed to the lack of successful clinical trials.

Current methods for generating gutless adenovirus vectors start with the rescue of the gutless virus by transfecting plasmid DNA into helper cells. However, plasmid DNA is poorly infectious, and the initial titers obtained upon transfection are generally too low for an efficient amplification of the gutless virus. The process necessitates a series of time-consuming and labor-intense virus passages, with the consequence that the gutless virus preparations are often contaminated with products of recombination. It becomes clear that the lower the number of gutless viral particles produced in rescue, the higher the number of passages required before purification. Therefore a technique which can enhance the rescue of virus from plasmid DNA is needed.

The present disclosure addresses this problem as it provides a method for binding adenovirus terminal protein to linear DNA.

To improve the critical step of gutless virus rescue, the present invention has utilized the adenovirus terminal protein. In the virion, the linear genomic DNA is linked at each end to a 55 kDa terminal protein (TP). To increase the infectivity of plasmid DNAs, a method has been disclosed to link the TP to plasmid DNA ends. Because the TP is bound to DNA in a very specific way, which would be very difficult to achieve in routine, the TP is purified from virions as a complex with a short stretch of DNA (the inverted terminal repeat—ITR), that is linked to the ends of linearized plasmid DNA by a DNA ligation reaction. This methodology is referred to hereafter as the "TP-ITR" method.

The use of the TP to generate gutless adenovirus vectors from plasmid DNA translates both in a shorter virus recovery time and in higher virus yields when compared to methods that use plasmid DNA devoid of TP. By considerably improving the first rescue step in the construction of gutless vectors, the TP-ITR method decreases the number of passages that are required to obtain high-titer virus preparations. Thus the method speeds up the process, and also leads to a superior product by decreasing the possibility of gutless vector recombination.

There are at least four advantages of using the TP-ITR method for producing gutless adenovirus. First, the binding of the terminal protein (TP) to the linearized plasmid DNA used to generate the gutless virus is consistently reproducible and efficient. The TP is indeed provided as a covalent complex with the inverted terminal repeat (ITR), which is linked to the gutless genome by a DNA ligation. Because both DNAs have complementary sticky ends which are not symmetrical, the formation of TP-ITR dimers or the recircularization of the gutless genome is prohibited, and ligation of the TP-ITR to the gutless genome can be completed at almost 100% efficiency in just one hour, using a T4 DNA ligase.

A second advantage is that very high titers of gutless virus can be obtained upon transfecting the gutless plasmid and helper plasmid DNAs into helper cells (passage "0"). Utilizing 2 μg of gutless plasmid can generate up to $1.5 \times 10^8$ gutless virus particles, that is at least 2800-fold greater than methods that do not incorporate the TP-ITR.

A third advantage is that the virus suspension obtained from passage "0" is virtually free of helper virus. Indeed the genome of the helper virus used in the transfection step can be deleted from the packaging signal, and as a result can share no homology with the genome of the gutless virus (except for the ITR), and would not generate replication-competent adenovirus (RCA) by homologous recombination.

Finally the TP-ITR complex is purified from the helper virus itself, which is used downstream to amplify the virus (passages 1, 2, . . . ). This drops any concern about potential contamination of the TP-ITR preparations with the source virus, since this latter is added anyway to the gutless virus extract later during the amplification.

Figure 1:
FIG. 1 shows agarose gel electrophoresis analysis of the ligations of pAd337/SfiI and pAd1081/SfiI with TP-ITR. The 2724 base pair and 914 base pair fragments are shifted up. In lane 4 (from left), the intensities of the 914 base pair and 1024 base pair fragments are about equal indicating the ligation efficiency is approximately 50%.

(terminal fragments in bold face). Lanes 1-4: 0, 8, 16 and 32 µL of TP-ITR from pAd337/SfiI, respectively; Lane 5: Mw markers; Lanes 6-9: 0, 8, 16 and 32 µL of TP-ITR from pAd1081/SfiI, respectively.

SUMMARY

The present disclosure relates to methods for adenoviral vectors synthesis. More specifically, the disclosure relates to methods for binding adenovirus terminal protein to linear DNA.

In one aspect, the present disclosure provides a method for binding adenovirus terminal protein to linear DNA comprising: (a) amplification of a virus, wherein the virus contains adenovirus terminal protein bound to viral DNA, wherein the viral DNA is an inverted terminal repeat DNA sequence, wherein the adenovirus terminal protein bound to the inverted terminal repeat DNA sequence forms an adenovirus terminal protein-inverted terminal repeat DNA sequence complex; (b) purification of the adenovirus terminal protein-inverted terminal repeat DNA sequence complex from the virus; and, (c) DNA ligation of the adenovirus terminal protein-inverted terminal repeat DNA sequence complex to linear DNA by DNA ligase. According to one embodiment of the method, the virus is an adenovirus. According to another embodiment, the virus is a helper virus used for gutless virus production. According to another embodiment, the inverted terminal repeat DNA sequence is about 100 base pairs. According to another embodiment, the inverted terminal repeat DNA sequence is terminated with the terminal protein on one end of the inverted terminal repeat DNA and with a non-palindromic sticky end on the other end of the inverted terminal repeat DNA. According to another embodiment, the adenovirus terminal protein-inverted repeat DNA sequence complex is purified from cells containing replicating virus. According to another embodiment, the linear DNA is used to make adenovirus vectors. According to another embodiment, the adenovirus vector is a gutless vector. According to another embodiment, the linear DNA is terminated with a non-palindromic sticky end.

In another aspect, the present disclosure further provides a recombinant adenovirus from which the adenovirus terminal protein can be purified with an inverted terminal repeat DNA sequence comprising one or a group of endonuclease sites which produce identical non-palindromic sticky ends adjacent to inverted terminal repeat DNA sequences, a packaging signal, a deletion in the E1 region, a stuffer DNA fragment in the E3 or E4 region, wherein the stuffer fragment increases the size of the viral genome to about 36 kilobases, wherein the recombinant adenovirus is a helper-independent adenovirus, and wherein the helper-independent virus can be deleted for at least one viral gene. According to one embodiment, the group of endonuclease sites comprises a DraIII restriction enzyme site and a SfiI restriction enzyme site. According to another embodiment, one or more of the DraIII restriction enzyme sites that are present naturally in the adenovirus genome have been mutated. According to another embodiment, the group of endonuclease sites comprises a BstXI restriction enzyme site and an I-SceI restriction enzyme site. According to another embodiment, one or more of the BstXI restriction enzyme sites that are present naturally in the adenovirus genome have been mutated. According to another embodiment, the packaging signal has minimal homology to the packaging signal of a gutless plasmid. According to another embodiment, the stuffer DNA does not encode for a protein or a regulatory sequence. According to another embodiment, the stuffer DNA does not share homology with the chromosomes of the cell where the virus is propagated, the chromosomes of the cell to which it is targeted, or the gutless virus genome.

In another aspect, the present disclosure further provides a recombinant adenovirus from which the adenovirus terminal protein can be purified with an inverted terminal repeat DNA sequence comprising a deletion of the E1 region, a DraIII restriction enzyme site and a SfiI restriction enzyme site adjacent to inverted terminal repeat DNA sequences, a packaging signal, a pair of Lox sites or a pair Frt sites flanking the packaging signal, a stuffer DNA fragment in the E3 or E4 region, wherein the stuffer fragment increases the size of the viral genome to about 36 kilobases, wherein the recombinant adenovirus is a helper-independent adenovirus, and wherein the helper-independent virus can be deleted for at least one viral gene. According to one embodiment of the recombinant adenovirus, the recombinant adenovirus is replication-deficient. According to another embodiment, the recombinant adenovirus packaging signal is a wild-type packaging signal. According to another embodiment, the packaging signal has minimal homology to the packaging signal of a gutless plasmid. According to another embodiment, one or more of the DraIII sites naturally present in the viral genome has been mutated. According to another embodiment, the stuffer DNA does not encode for a protein or a regulatory sequence. According to another embodiment, the stuffer DNA does not share homology with the chromosomes of the cell where the virus is propagated, the chromosomes of the cell to which it is targeted, or the gutless virus genome. According to another embodiment, the recombinant adenovirus further comprises a plurality of restriction enzyme sites. According to another embodiment, the restriction enzyme site is BstXI. According to another embodiment, the recombinant adenovirus further comprises homing endonuclease sites. In some such embodiments, the homing endonuclease is I-SceI.

DETAILED DESCRIPTION

Glossary

Unless defined otherwise, all technical and scientific terms used herein have the same meaning as commonly understood by one of ordinary skill in the art to which this disclosure belongs. Generally, the nomenclature used herein and the laboratory procedures in cell culture, molecular genetics, and nucleic acid chemistry and hybridization described below are those well known and commonly employed in the art. Standard techniques are used for recombinant nucleic acid methods, polynucleotide synthesis, and microbial culture and transformation (e.g., electroporation, lipofection). Generally, enzymatic reactions and purification steps are performed according to the manufacturer's specifications. The techniques and procedures are generally performed according to conventional methods in the art and various general references (see generally, Sambrook et al. Molecular Cloning: A Laboratory Manual, 2d ed. (1989) Cold Spring Harbor Laboratory Press, Cold Spring Harbor, N.Y., which is incorporated herein by reference) which are provided throughout this document. Units, prefixes, and symbols may be denoted in their SI accepted form. Unless otherwise indicated, nucleic acids are written left to right in 5' to 3' orientation; amino acid sequences are written left to right in amino to carboxyl orientation, respectively. Numeric ranges are inclusive of the numbers defining the range and include each integer within the defined range. Amino acids may be referred to herein by either their commonly known three letter symbols or by the one-letter symbols recommended by the IUPAC-IUB Biochemical nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms (5.sup.th edition, 1993). As employed throughout the disclosure, the following terms, unless otherwise indicated, shall be understood to have the following meanings and are more fully defined by reference to the specification as a whole:

The term "adenovirus" as used herein refers to the non-enveloped icosahedral viruses composed of a nucleocapsid and a double-stranded linear DNA. Adenoviruses represent the largest non-enveloped viruses and are stable to chemical or physical agents and adverse pH conditions. The adenovirus genome is a non-segmented dsDNA about 30-38 kilobases long. The viral genome has a terminal 55 kilodalton (kDA) protein associated with each of the 5' ends of the linear dsDNA which are used as primers in viral replication and ensure the ends of the virus linear genome are adequately replicated.

The term "amplification" as used herein refers to the usually massive replication of genetic material.

The term "bound" as used herein refers to combine with, form a chemical bond with, or be taken up by as, for example, but not limited to, an enzyme with its substrate.

The term "complex" as used herein refers to an entity composed of molecules in which the constituents maintain much of their chemical identity, such as, for example, but not limited to, a receptor-hormone complex, an enzyme-substrate complex, a terminal protein-inverted DNA complex, or a terminal protein-inverted terminal repeat complex.

The term "delete" or "deleted" as used herein refers to expunging, erasing, or removing.

The term "E1 region" as used herein refers to a group of genes present in the adenovirus genome. These genes, such as, but not limited to, E1a and E1b, are expressed in the early phase of virus replication and activate the expression of the other viral genes.

The term "E3 region" as used herein refers to a group of genes that are present in the adenovirus genome and are expressed in the early phase of the virus replication cycle. These genes express proteins that interact with the host immune system. They are not necessary for virus replication in vitro, and therefore may be deleted in adenovirus vectors.

The term "E4 region" as used herein refers to a group of genes that are present in the adenovirus genome next to the right ITR, and are expressed in the early phase of the virus replication cycle.

The E4 region includes at least 7 ORFs. The products of the E4 region promote viral gene expression and replication, interact with host cell components, and participate in lytic infection and oncogenesis.

The term "gutless" or "gutted" vectors as used herein refers to a vector being devoid of all viral sequences, except those required for replication and packaging, such as, but not limited to, the inverted terminal repeats (ITRs) and the packaging signal (ψ). Gutless vectors require viral proteins supplied in trans by a helper virus. Gutted Ad vectors are also referred to as "helper-dependent" adenoviruses because they need a helper adenovirus that carries all coding regions. They are also called "high-capacity" adenoviruses because they can accommodate up to 36 kilobases of DNA. They are also referred to as "mini", "fully-deleted", "Δ", or "pseudo". Briefly, the gutless adenovirus only keeps the 5' and 3' inverted terminal repeats (ITRs) and the packaging signal (ψ) from the wild-type adenovirus. As vector capsids package efficiently only 75-105% of the whole adenovirus genome, and as therapeutic expression cassettes usually do not match up to 36 kb, there is a need to use "stuffer" DNA in order to complete the genome size for encapsidation.

The term "gutless plasmid" as used herein refers to a plasmid that contains the entire genome of a gutless virus. Typically, the gutless plasmid is linearized with an enzyme that cuts outside the inverted terminal repeats before being transfected into cells in order to rescue virus particles.

The term "helper-independent" as used herein refers to an adenovirus that does not need the presence of a helper virus for its replication. These adenoviruses include "first-generation" and "second-generation" adenovirus vectors. A first-generation adenovirus vector refers to an adenovirus in which exogenous DNA replaces the E1 region, or optionally the E3 region, or optionally both the E1 and E3 region. A second-generation adenovirus vector refers to a first-generation adenovirus vector, which, in addition to the E1 and E3 regions, contains additional deletions in the E2 region, the E4 region, or any other region of the adenovirus genome, or a combination thereof.

The term "helper virus" as used herein refers to virus used when producing copies of a helper-dependent viral vector which does not have the ability to replicate on its own. The helper virus is used to co-infect cells alongside the gutless virus and provides the necessary enzymes for replication of the genome of the gutless virus and the structural proteins necessary for the assembly of the gutless virus capsid.

The term "helper plasmid" as used herein refers to a plasmid that contains the entire genome of a helper virus used to generate gutless virus. Typically, the helper plasmid is linearized with an enzyme that cuts outside the inverted terminal repeats. It may then be transfected into cells in order to rescue virus particles.

The term "homing endonuclease" refers to double stranded DNases that have large, asymmetric recognition sites (12-40 base pairs) and coding sequences that are usually embedded in either introns or inteins. Introns are spliced out of precursor RNAs, while inteins are spliced out of precursor proteins. Homing endonucleases are named using conventions similar to those of restriction endonucleases with intron-encoded endonucleases containing the prefix, "I-" and intein endonucleases containing the prefix, "PI-". Homing endonuclease recognition sites are extremely rare. For example, an 18 base pair recognition sequence will occur only once in every $7\times10^{10}$ base pairs of random sequence. This is equivalent to only one site in 20 mammalian-sized genomes. However, unlike standard restriction endonucleases, homing endonucleases tolerate some sequence degeneracy within their recognition sequence. As a result, their observed sequence specificity is typically in the range of 10-12 base pairs. Homing endonucleases do not have stringently-defined recognition sequences in the way that restriction enzymes do. That is, single base changes do not abolish cleavage but reduce its efficiency to variable extents. The precise boundary of required bases is generally not known. I-SceI is a site-specific homing endonuclease.

The term "homology" as used herein refers to the situation where nucleic acid or protein sequences are similar.

The term "inverted terminal repeat" as used herein refers to DNA sequences located at the left and right termini of the adenovirus genome. These sequences are identical to each other, but placed in opposite directions. The length of the inverted terminal repeats of adenoviruses vary from about 50 bp to about 170 bp, depending on the serotype of the virus. The inverted terminal repeats contain a number of different cis-acting elements required for viral growth, such as the core origin of viral DNA replication and enhancer elements for the activation of the E1 region.

The term "ligase" as used herein refers to an enzyme that can link together DNA strands that have double-strand breaks. The common commercially available DNA ligases are derived from T4, Escherichia coli or other bacteria.

The term "linear DNA" as used herein refers to non-circularized DNA molecules.

The term "minimum homology" as used herein refers to the smallest length of homology required for efficient recombination. Generally, intramolecular homologous recombination decreases linearly as length of homology is progressively decreased, however, the decrease is more rapid after the length of homology goes below the minimum.

The term "multiple cloning site," also referred to as an "MCS" or a "polylinker" refers to a short segment of DNA which contains many (usually 20+) sites recognized by restriction enzymes or other endonucleases such as homing endonucleases.

The term "mutation" as used herein refers to a change in a nucleotide sequence that departs form the wild-type sequence. There are several types of mutations. Point mutations, often caused by chemicals or malfunction of DNA replication, exchange a single nucleotide for another. Most common is the transition that exchanges a purine for a purine (A⇌G) or a pyrimidine for a pyrimidine, (C⇌T). A transition can be caused by nitrous acid, base mis-pairing, or mutagenic base analogs such as 5-bromo-2-deoxyuridine (BrdU). Less common is a transversion, which exchanges a purine for a pyrimidine or a pyrimidine for a purine (C/T⇌A/G). A point mutation can be reversed by another point mutation, in which the nucleotide is changed back to its original state (true reversion) or by second-site reversion (a complementary mutation elsewhere that results in regained gene functionality). These changes are classified as transitions or transversions. An example of a transversion is adenine (A) being converted into a cytosine (C). There are also many other examples that can be found. Point mutations that occur within the protein coding region of a gene may be classified into three kinds, depending upon what the erroneous codon codes for: i) silent mutations: which code for the same amino acid; ii) missense mutations: which code for a different amino acid; and iii) nonsense mutations: which code for a stop and can truncate the protein. Insertions add one or more extra nucleotides into the DNA. They are usually caused by transposable elements, or errors during replication of repeating elements (e.g. AT repeats). Insertions in the coding region of a gene may alter splicing of the mRNA (splice site mutation), or cause a shift in the reading frame (frameshift), both of which can significantly alter the gene product. Insertions can be reverted by excision of the transposable element. Deletions remove one or more nucleotides from the DNA. Like insertions, these mutations can alter the reading frame of the gene. They are generally irreversible: though exactly the same sequence might theoretically be restored by an insertion, transposable elements able to revert a very short deletion (say 1-2 bases) in any location are either highly unlikely to exist or do not exist at all. Note that a deletion is not the exact opposite of an insertion: the former is quite random while the latter consists of a specific sequence inserting at locations that are not entirely random or even quite narrowly defined. Mutations may also affect chromosomal structure, including: amplifications (or gene duplications) leading to multiple copies of all chromosomal regions, increasing the dosage of the genes located within them; deletions of large chromosomal regions, leading to loss of the genes within those regions; mutations whose effect is to juxtapose previously separate pieces of DNA, potentially bringing together separate genes to form functionally distinct fusion genes (e.g. bcr-abl). These include: chromosomal translocations: interchange of genetic parts from nonhomologous chromosomes; interstitial deletions: an intra-chromosomal deletion that removes a segment of DNA from a single chromosome, thereby apposing previously distant genes; chromosomal inversions: reversing the orientation of a chromosomal segment; and loss of heterozygosity: loss of one allele, either by a deletion or recombination event, in an organism that previously had two different alleles.

The term "naturally" as used herein refers to as found in nature; wild-type; innately or inherently.

The terms "non-palindromic" and "non-symmetrical" are used interchangeably and as used herein refer to a sequence that is not equal to its complementary sequence read backwards The term "nucleic acid" refers to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

The term "packaging signal" as used herein refers to a nucleotide sequence that is present in the virus genome and is necessary for the incorporation of the virus genome inside the virus capsid during virus assembly. The packaging signal of adenovirus is naturally located at the left-end terminus, downstream from the left inverted terminal repeat. It may be denoted as "ψ".

The term "palindromic" as used herein refers to a sequence that is equal to its complementary sequence read backwards.

The term "pHD" as used herein refers to a plasmid that contains the sequence of a "Helper-Dependent" (HD) or gutless adenovirus. The sequence of the gutless virus is usually contained between two recognition sites of a rare-cutter restriction enzyme or a homing endonuclease. The digestion of the pHD plasmid with these enzymes releases the gutless viral genome from the vector and allows rescue of the virus upon transfection in helper cells.

The term "pHV" as used herein refers to a plasmid that contains the sequence of a helper virus (HV) used to produce gutless adenovirus. The sequence of the helper virus is usually contained between two recognition sites of a rare-cutter restriction enzyme or a homing endonuclease. The digestion of the pHV plasmid with these enzymes releases the gutless viral genome from the vector and allows rescue of the virus upon transfection in helper cells.

The term "plasmid" as used herein refers to an extra-chromosomal DNA molecule separate from the chromosomal DNA which is capable of replicating independently of the chromosomal DNA. In many cases, it is circular and double-stranded.

The term "propagate" or "propagated" as used herein refers to reproduce, multiply, or to increase in number, amount or extent by any process.

The term "purification" as used herein refers to the process of purifying or to free from foreign, extraneous, or objectionable elements.

The term "regulatory sequence" (also called regulatory region or regulatory element) as used herein refers to a promoter, enhancer or other segment of DNA where regulatory proteins such as transcription factors bind preferentially. They control gene expression and thus protein expression.

The term "recombinase" as used herein refers to an enzyme that catalyzes genetic recombination. A recombinase enzyme catalyzes the exchange of short pieces of DNA between two long DNA strands, particularly the exchange of homologous regions between the paired maternal and paternal chromosomes.

The term "restriction enzyme" (or restriction endonuclease) refers to an enzyme that cuts double-stranded DNA. The enzyme makes two incisions, one through each of the phosphate backbones of the double helix without damaging the bases. Restriction enzymes are classified biochemically into four types, designated Type 1, Type II, Type III, and Type IV. In Type I and Type III systems, both the methylase and restriction activities are carried out by a single large enzyme complex. Although these enzymes recognize specific DNA sequences, the sites of actual cleavage are at variable distances from these recognition sites, and can be hundreds of bases away. Both require ATP for their proper function. In Type II systems, the restriction enzyme is independent of its methylase, and cleavage occurs at very specific sites that are within or close to the recognition sequence. Type II enzymes are further classified according to their recognition site. Most Type II enzymes cut palindromic DNA sequences, while Type IIa enzymes recognize non-palindromic sequences and cleavage outside of the recognition site. Type IIb enzymes cut sequences twice at both sites outside of the recognition sequence. In Type IV systems, the restriction enzymes target only methylated DNA. BstXI is a restriction enzyme.

The term "restriction sites" or "restriction recognition sites" refer to particular sequences of nucleotides that are recognized by restriction enzymes as sites to cut the DNA molecule. The sites are generally, but not necessarily, palindromic, (because restriction enzymes usually bind as homodimers) and a particular enzyme may cut between two nucleotides within its recognition site, or somewhere nearby.

The term "replication" or "replicating" as used herein refers to making an identical copy of an object such as, for example, but not limited to, a virus particle.

The term "replication deficient" as used herein refers to the characteristic of a virus that is unable to replicate in a natural environment. A replication deficient virus is a virus that has been deleted of one or more of the genes that are essential for its replication, such as, for example, but not limited to, the E1 genes. Replication deficient viruses can be propagated in a laboratory in cell lines that express the deleted genes.

The term "rescue" as used herein refers to the process in which viruses are prepared initially in plasmid form and must be converted to replicating viral form. The process may be referred to as rescue of the vector. The term can be applied to all categories of adenoviral vectors, including first-generation, second-generation, and gutless vectors.

The term "source" as used herein refers to a material from which a component can be purified. For instance, "a helper virus can be a source for the TP-ITR complex" means that the TP-ITR complex can be purified from a helper virus.

The term "sticky end" as used herein refers to non-blunt ends of a dsDNA molecule that are often created by restriction endonucleases when they cut DNA. Sticky ends may result when two DNA strands are cut, for example, but not limited to, four base pairs from each other creating a four base 3' overhang in the other molecule and a complementary overhang in the other; these ends are called 'sticky ends' or 'cohesive' since they are easily joined back together by a ligase.

The term "stuffer fragment" as used herein refers to a DNA sequence that is inserted into another DNA sequence in order to increase its size. For example, a stuffer fragment can be inserted inside the adenovirus genome to increase its size to about 36 kb. Stuffer fragments usually do not code for any protein nor contain regulatory elements for gene expression, such as transcriptional enhancers or RNA splice sites.

The term "target" or "targeted" as used herein refers to a biological entity, such as, for example, but not limited to, a protein, cell, organ, or nucleic acid, whose activity can be modified by an external stimulus. Depending upon the nature of the stimulus, there may be no direct change in the target, or a conformational change in the target may be induced.

The term "terminal protein" as used herein refers to a protein bound to the end of a nucleotide sequence. The adenovirus terminal protein is covalently bound to the 5'-end of the viral genome.

The term "titer" as used herein refers to the result of a laboratory test that employs serial dilution to obtain approximate quantitative information from an analytical procedure that inherently only evaluates as positive or negative. The titer corresponds to the highest dilution factor that still yields a positive reading. Many traditional serological tests, such as hemagglutination or complement fixation, employ this principle.

The term "vector" refers to a nucleic acid used in transfection of a host cell and into which can be inserted a polynucleotide. Vectors are frequently replicons. Expression vectors permit transcription of a nucleic acid inserted therein. Some common vectors include, but are not limited to, plasmids, cosmids, viruses, phages, recombinant expression cassettes, and transposons. The term "vector" may also refer to an element which aids in the transfer of a gene from one location to another.

The term "viral DNA" as used herein refers to a sequence of DNA that is found in virus particles.

The term "viral genome" as used herein refers to the totality of the DNA that is found in virus particles, and that contains all the elements necessary for virus replication. The genome is replicated and transmitted to the virus progeny at each cycle of virus replication.

The term "virions" as used herein refers to a viral particle. Each virion consists of genetic material within a protective protein capsid.

The term "wild-type" as used herein refers to the typical form of an organism, strain, gene, protein, nucleic acid, or characteristic as it occurs in nature. Wild-type refers to the most common phenotype in the natural population. The terms "wild-type" and "naturally occurring" are used interchangeably.

In one aspect, the present invention provides methods for binding adenovirus terminal protein to linear DNA. The method comprises several steps. First, virus containing adenovirus terminal protein bound to inverted terminal repeat viral DNA sequence is amplified. Second, the adenovirus terminal protein-inverted terminal repeat viral DNA complex is then purified away from the virus. Third, the adenovirus terminal protein-inverted terminal repeat viral DNA complex is ligated to linear DNA utilizing DNA ligase.

In one embodiment, the virus is an adenovirus. In another embodiment, the adenovirus is a first-generation adenovirus vector. In another embodiment, the first-generation adenovirus vector is Ad299 or Ad324. In another embodiment, the virus is a helper virus used for gutless virus production. In another embodiment, the helper virus is Ad336. In another embodiment, the virus has at least one terminal protein. In another embodiment, the virus has a left inverted terminal repeat and/or a right inverted terminal repeat. In another embodiment, the virus genome has at least one DraIII restriction enzyme site. In another embodiment, the virus has at least one Frt recombination site. In another embodiment, the virus has a ψ region. In another embodiment, the virus has an ΔE1 region. In another embodiment, the virus has an E4 region. In another embodiment, the virus has a WT-E3 region. In another embodiment, the virus has stuffer λ DNA. In another embodiment, stuffer λ DNA increases the viral genome size to about 36 kilobases. In another embodiment, the virus has immediately downstream from the left and right ITRs DraII restriction enzyme sites which generate sticky ends identical to those generated by the SfiI sites present in plasmids pHD and pHV. In another embodiment, flanking either side of the packaging signal are Frt recombination sites. In another embodiment, Lox sites and/or tandem lox-Frt sites are used on either side of the packaging signal in other plasmids. In another embodiment, the stuffer DNA fragment is about 3.1 kilobases. In another embodiment, the number of DraII sites within the helper virus genome is reduced with 3 point mutations.

In another embodiment, the virus is amplified in human cell lines. In another embodiment, the virus is amplified in 293 cells. In another embodiment, the virus is amplified in 293 cells grown in iron-free medium. In another embodiment, the Ad324 virus is amplified in 293 cells with a yield of about 40,000 VP/cell. In another embodiment, the Ad336 helper virus is amplified in 293 cells with a yield of about 10,000 VP/cell.

In another embodiment, the DNA ligation of the adenovirus terminal protein-inverted terminal repeat DNA sequence complex to linear DNA is performed with DNA ligase. In another embodiment, the DNA ligase is T4 DNA ligase. In another embodiment, the DNA ligation efficiency of the adenovirus terminal protein-inverted terminal repeat DNA sequence complex to linear DNA is at least 35%. In another embodiment, the DNA ligation efficiency of the adenovirus terminal protein-inverted terminal repeat DNA sequence complex to linear DNA is at least 40%. In another embodiment, the DNA ligation efficiency of the adenovirus terminal protein-inverted terminal repeat DNA sequence complex to linear DNA is at least 50%. In another embodiment, the DNA ligation efficiency of the adenovirus terminal protein-inverted terminal repeat DNA sequence complex to linear DNA is about 100%.

In another embodiment, the virus is used as a helper for gutless virus production. In another embodiment, the gutless virus is Ad1081. In another embodiment, gutless virus production utilizes a plasmid containing the sequence of a gutless adenovirus genome flanked by SfiI restriction enzyme sites. In another embodiment, the plasmid is based on pGS46. In another embodiment the plasmid is called pHD. In another embodiment, the plasmid contains the first 440 bp from wild-type Ad5 genome. In another embodiment, the plasmid includes the left ITR and packaging signal. In another embodiment, the plasmid contains a 16 kb-long stuffer DNA sequence from the HPRT locus. In another embodiment, the plasmid contains a cassette expressing β-galactosidase under the control of a CMV promoter. In another embodiment, the plasmid contains a SV40 poly-adenylation signal. In another embodiment, the plasmid contains a 9 kb-long stuffer DNA sequence from cosmid C346. In another embodiment, the plasmid contains the right ITR (corresponding to sequence nt 35818 to 35935 in Ad5 genome). In another embodiment, two SfiI sites are inserted into the gutless genome: one between the left ITR and the packaging signal, and a second between the right ITR and cosmid C346 sequence. These SfiI sites generate sticky ends that are complementary with those presents on the TP-ITR complex.

In another embodiment, the present invention provides a method for generating HD viruses. The helper virus is the virus from which the TP-ITR is purified. In addition, the first step of the process, i.e. the co-transfection of the gutless plasmid and helper plasmid into 293 cells allows use a variant of the helper plasmid, from which the packaging signal has been deleted. In another embodiment the present invention allows for producing gutless virus preparations that do not contain helper virus particles.

In another embodiment, the titer of gutless virus obtained using the terminal protein-inverted terminal repeat complex is at least 1 order of magnitude higher than the titer obtained using the same vectors lacking terminal protein-inverted terminal repeats complex. In another embodiment, the titer of gutless virus obtained using the terminal protein-inverted terminal repeat complex is at least 2 orders of magnitude higher than the titer obtained using the same vectors lacking terminal protein-inverted terminal repeats complex. In another embodiment, the titer of gutless virus obtained using the terminal protein-inverted terminal repeat complex is at least 3 orders of magnitude higher than the titer obtained using the same vectors lacking terminal protein-inverted terminal repeats complex.

In another embodiment, the inverted terminal repeat sequence has about 1 to 200 base pairs. In another embodiment, the inverted terminal repeat sequence has about 25 to 175 base pairs. In another embodiment, the inverted terminal repeat sequence has about 50 to 150 base pairs. In another embodiment, the inverted terminal repeat sequence has about 100 base pairs.

In another embodiment, the inverted terminal repeat sequence is terminated with a sticky end. In another embodiment, the inverted terminal repeat sequence is terminated with a non-palindromic sticky end.

In another embodiment, the adenovirus terminal protein-inverted terminal repeat complex is purified by chromatography. In another embodiment, the adenovirus terminal protein-inverted terminal repeat complex is purified by size-exclusion chromatography, such as, for example, but not limited to, Sepharose 4FF. In another embodiment, the adenovirus terminal protein-inverted terminal repeat complex is purified by Hydrophobic Interaction Chromatography. In another embodiment, the adenovirus terminal protein-inverted terminal repeat complex is purified by anion-exchange chromatography.

In another aspect, the present invention further provides a recombinant adenovirus. In one embodiment the recombinant adenovirus comprises the adenovirus terminal protein. In another embodiment, the adenovirus terminal protein can be purified with an inverted terminal repeat DNA sequence. In another embodiment, the recombinant adenovirus comprises a deletion of the E1 region. In another embodiment, the recombinant adenovirus comprises a DraIII restriction enzyme site adjacent to inverted terminal repeat DNA sequences. In another embodiment, the recombinant adenovirus comprises a SfiI restriction enzyme site adjacent to inverted terminal repeat DNA sequences. In another embodiment, the recombinant adenovirus comprises both a DraIII site and a SfiI site adjacent to inverted terminal repeat DNA sequences. In another embodiment, the DraIII and SfiI sites adjacent to inverted terminal repeat DNA sequences generate identical non-palindromic sticky ends. In another embodiment, the recombinant adenovirus comprises a BstXI restriction enzyme site adjacent to inverted terminal repeat DNA sequences. In another embodiment, the recombinant adenovirus comprises an I-SceI endonuclease site adjacent to inverted terminal repeat DNA sequences. In another embodiment, the recombinant adenovirus comprises both a BstXI restriction site and an I-SceI endonuclease site adjacent to inverted terminal repeat DNA sequences. In another embodiment, the BstXI and I-SceI sites adjacent to inverted terminal repeat DNA sequences generate identical non-palindromic sticky ends. In another embodiment, the recombinant adenovirus comprises a packaging signal. In another embodiment, the recombinant adenovirus comprises a stuffer DNA fragment in the E3 region. In another embodiment, the recombinant adenovirus comprises a stuffer DNA fragment in the E4 region. In another embodiment, the recombinant adenovirus comprises a pair of Lox sites flanking the packaging signal. In another embodiment, the recombinant adenovirus comprises a pair of Frt sites flanking the packaging signal. In another embodiment, the stuffer DNA increases the size of the viral genome to about 36 kilobases. In another embodiment, the recombinant adenovirus is a helper-independent adenovirus. In another embodiment, the helper-independent virus can be deleted for at least one viral gene.

General Techniques

General techniques in molecular genetics and genetic engineering useful in the present invention are described in the current editions of Molecular Cloning: A Laboratory Manual (Sambrook et al., Cold Spring Harbor); Gene Transfer Vectors for Mammalian Cells (Miller and Calos, eds.); and Current Protocols in Molecular Biology (Ausubel et al., eds., Wiley & Sons). Cell biology, protein chemistry, and antibody techniques can be found in Current Protocols in Protein Science (Colligan et al., eds.); Current Protocols in Cell Biology (Bonifacino et al., Wiley & Sons) and Current Protocols in Immunology (Colligan et al., eds., Wiley & Sons). Reagents, cloning vectors and kits for genetic manipulation are available from commercial vendors such as BioRad, Stratagene, Invitrogen, ClonTech, and Sigma-Aldrich Co.

Cell culture methods useful in the present invention are described generally in the current edition of Culture of Animal Cells: A Manual of Basic Technique (Freshney, ed., Wiley & Sons); General Techniques of Cell Culture (Harrison and Rae, Cambridge University Press); and Embryonic Stem Cells: Methods and Protocols (Turksen, ed., Human Press). Other relevant texts are Creating High Performance Culture (Aroselli, Hu. Res. Dev. Pr., 1996) and Limits to Growth (Meadows, et al., Universe Publ., 1974). Tissue culture supplies and reagents are available from commercial vendors such as Gibco/BRL, Nalgene-Nunc International, Sigma Chemical Co., and ICN Biomedicals.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and" and "the" include the plural references unless the context clearly dictates otherwise. All technical and scientific terms used herein have the same meaning.

Publications discussed herein are provided solely for their disclosure prior to the filing date of the present application. Nothing herein is to be construed as an admission that the present invention is not entitled to antedate such publication by virtue of prior invention. Further, dates of publication provided may be different from the actual publication dates which may need to be independently confirmed.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure the accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Comparison of Infectivity of Ad DNA Extracted from Virions with DNA Obtained from a Plasmid A comparison of the infectivity of an adenoviral (Ad) DNA extracted from virions with the same DNA obtained from a plasmid was performed. pAd288lacZ is a 44 kb plasmid that contains a full-length Ad5 genome with a cassette expressing the *E. coli*β-galactosidase in place of the E1 region. pAd288lacZ was linearized with PacI and transfected into 293 cells. Virus was recovered, amplified and purified twice on CsCl gradient. The viral genomic DNA, linked to the terminal protein, was extracted from viral particles using guanidinium hydrochloride, and further purified on CsCl gradient as previously described (Cauthen, A. and Spindler, K. in: *Adenovirus methods and protocols* (ed W. S. M. Wold) Humana Press, 85-103 (1999)), incorporated herein by reference in its entirety). The presence of the terminal protein bound to the viral DNA was verified by comparing, on agarose gel, the migration of the DNA before and after treatment with proteinase K. Half a microgram viral DNA, or PacI-digested pAd288lacZ were transfected into 293 cells. Five days after transfection, cells and medium were harvested and virus was released by 3 freeze-thaw cycles. After pelleting the cellular debris, the supernatant was used to infect confluent 293 cell monolayers. Infected cells were layered with solid medium, and viral plaques were counted 12 days later. The results show that, five days after transfection, cells transfected with the TP-linked viral DNA had generated 1.3 $10^6$ infectious particles, compared to 24 for the cells transfected with linear plasmid DNA. The TP-linked viral DNA was much more efficient in generating plaques than a similar plasmid DNA.

Example 2

Construction of a Helper Virus used as a Source of the TP-ITR Complex

This example describes the construction of a helper virus used as a source of the TP-ITR complex.

2.1. Construction of a helper virus used as a source of the TP-ITR complex.

The helper virus Ad336 was constructed by adding several elements on small plasmids carrying either the left end or the right end of the adenovirus genome, then combining the resulting plasmids together into a cosmid that contains the entire sequence of the helper virus genome.

2.2. Structure of the helper virus: features

Figure 4:
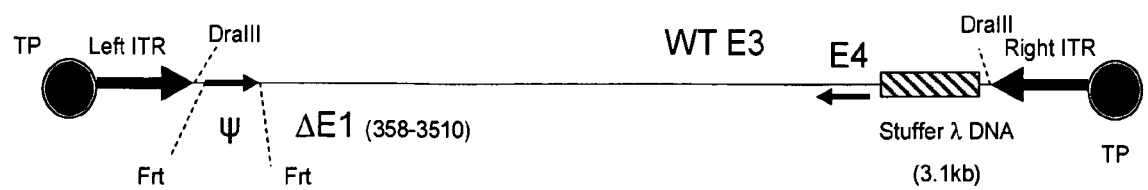
FIG. 4 shows the structure of helper virus Ad336. The virus is a source for the TP-ITR complex. From left, terminal protein (TP) (circle); left ITR; DraIII restriction enzyme site; Frt restriction enzyme site; ψ; Frt restriction enzyme site; ΔE1 (358-3510); WT E3; E4 (reverse direction); stuffer λ DNA (3.1 kilobases); DraIII restriction enzyme site; right ITR (reverse direction); terminal protein (circle).

FIG. 4 shows the structure of helper virus Ad336. The virus is a source for the TP-ITR complex. From left, terminal protein (TP) (circle); left ITR; DraIII restriction enzyme site; Frt recombination site; packaging signal ψ; Frt recombination site; ΔE1 (358-3510); WT E3; E4 (reverse direction);

stuffer λ DNA (3.1 kilobases); DraIII restriction enzyme site; right ITR (reverse direction); terminal protein (circle).

2.3. Immediately downstream from the left and right ITRs are DraIII restriction enzyme sites which generate sticky ends identical to those generated by the SfiI sites present in plasmids pHD and pHV.

The incorporation of DraIII at these locations provides advantages over potential SfiI sites located there including 1) when sticky ends generated by both enzymes are joined together neither site is recreated, thereby eliminating enzyme clean-up upon cleaving pHD plasmid with SfiI prior to the ligation with the TP-ITR; and 2) other DraIII sites are naturally present in the Ad336 genome. During excision of the TP-ITR from the Ad336 genome with DraIII, small DNA fragments are generated which decrease the viscosity of the digestion mixture and prevent back-pressure problems in the chromatography columns used for the TP-ITR purification scheme.

2.4. Flanking either side of the packaging signal are Frt recombination sites. The Ad336 is used as helper for generating HD viruses using a 293 cell-line expressing Flpe recombinase. Lox sites and tandem lox-Frt sites have also been used on either side of the packaging signal in other plasmids. They may be used to generate variants of Ad336 for use in Cre-expressing cell lines or either one.

2.5. E1 deletion (nt 356-3504) is incorporated to minimize the possibility of generating replication competent adenoviruses (RCA) upon recombination of the viral DNA with the adenoviral sequences inserted into the chromosome of the 293 cells.

2.6. A 3.1 kilobase stuffer DNA fragment is introduced between the right ITR and the promoter of the E4 region. The stuffer DNA contains sequences from the genome of phage Lambda, which has been shuffled in order to destroy the ORFs coding for the phage structural proteins. The insertion of the stuffer DNA into the genome of the helper virus at another place than the E1 region, such as the E4 region, prevents the generation of RCAs from the helper virus during the propagation of the virus in 293 cells. Re-introduction of E1 sequences into the E1-deleted region of the helper genome by recombination with the 293 cell chromosomal DNA is not viable as the genome of the recombinant would exceed the packaging capacity of the virus.

2.7. The number of DraIII sites naturally present throughout the genome are reduced with three point mutations thereby 1) preventing the generation of small DNA fragments upon DraIII digestion, 2) facilitating TP-ITR purification via anion exchange and 3) reducing 2-fold the amount of restriction enzyme needed to digest the helper genome.

2.8. Ad336 helper virus is functional in 293 FLPe cells

Excision of the packaging signal of Ad336, which is flanked by Frt sites, from the Ad336 genome in 293 cells expressing the FLPe recombinase was confirmed.

Figure 2:
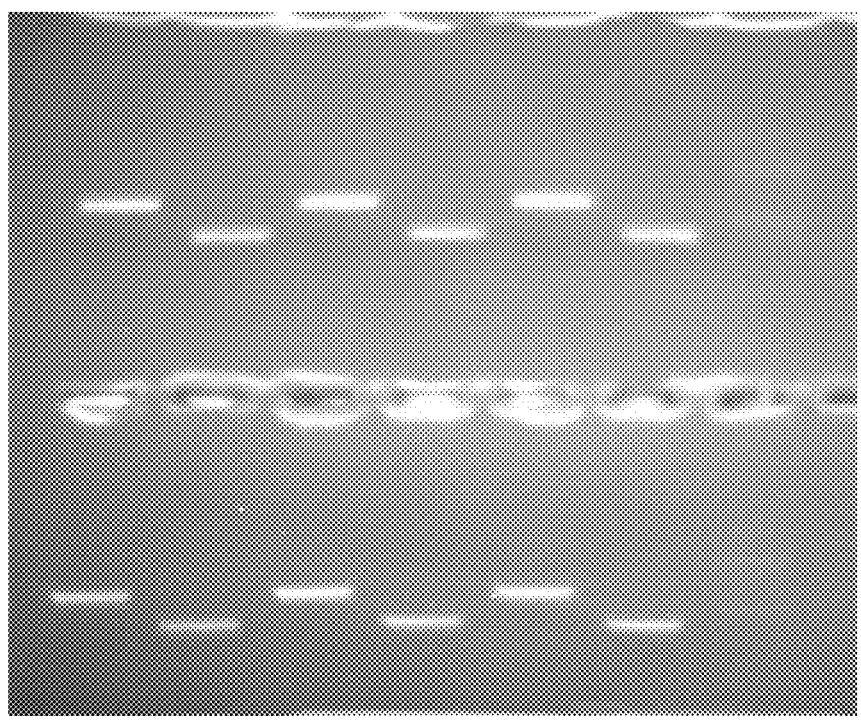
FIG. 2 shows excision of the packaging signal from Ad336 genome in 293 FLPe cells. 293 and 293-FLPe cells were infected with helper virus Ad336 at various MOI (from left: lanes 1 and 2: 30 MOI; lanes 3 and 4: 90 MOI; lanes 5 and 6: 270 MOI; lane 8: molecular markers (500 bp marker aligns with lanes 2, 4 and 6). One (top gel) or two days (bottom gel) after infection, viral DNA was extracted, and the region encompassing the packaging signal was amplified by PCR. PCR products were run on 1.5% agarose gel. Lanes 1, 3 and 5: FLPe(−) 293 cells; Lanes 2, 4 and 6: FLPe(+) 293 cells.

293 cells and 293-FLPe cells were infected with various concentrations of Ad336 (30, 90, 270 VP/cell). Cells were harvested 1 or 2 days later, and viral DNA was purified using the Hirt method. The region surrounding the packaging signal was amplified by PCR. FIG. 2 shows the presence of a 480 base pair fragment amplified from the viral DNA extracted from the 293-FLPe cells infected with Ad336, vs. 698 base pairs for the viral DNA extracted from the 293 cells. The approximate 200 base pair discrepancy corresponds to the excision of the packaging signal in 293-FLPe cells. The excision is very efficient, with samples from Day 1 and Day 2, as large 698 base pair fragments are not visible in the samples containing the 480 base pair fragments.

2.9 Ad336 helper virus yields about 10,000 VP/cell

The yield of Ad336 helper virus was compared with that of Ad324.

Figure 3A:
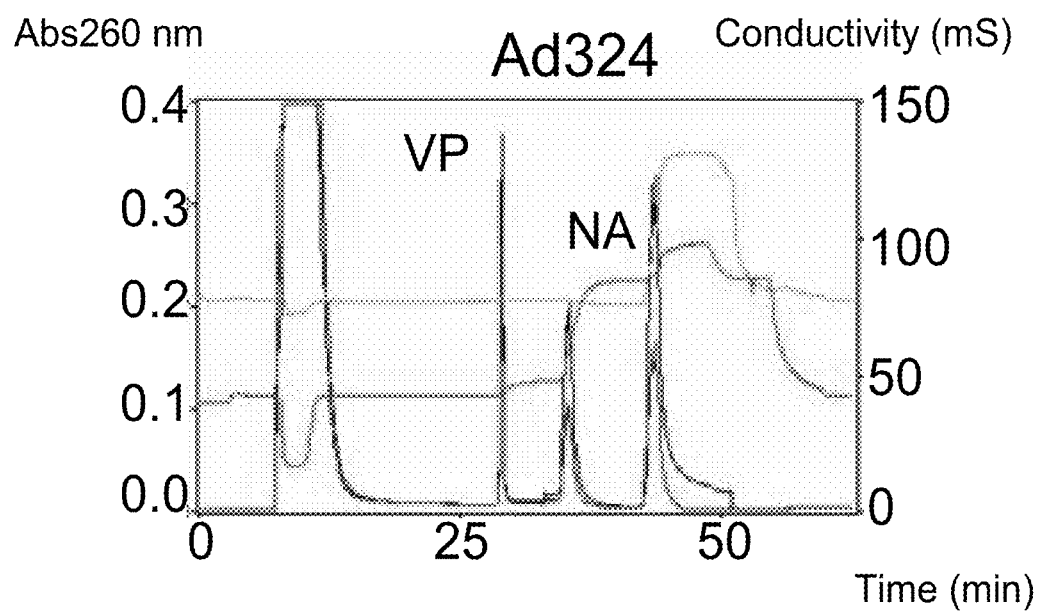
FIG. 3 shows a comparison of Ad324 (FIG. 3a) and Ad336 (FIG. 3b) virus particle yields in 293 cells. Monolayers of 293 cells were infected with equivalent amounts of infectious virus particles and harvested 2 or 3 days after infection. The viral output was analyzed by HPLC (1 ml HiTrap QSXL columns). Virus particles were eluted with a step gradient to 0.5 M NaCl (at approximately 27 minutes as shown in FIG. 3a, and approximately 26 minutes as shown in FIG. 3b, respectively) and nucleic acids (NA) were eluted (at approximately 45 minutes as shown in FIGS. 3a and 3b, respectively) with another step gradient to 1 M NaCl. The area under the Ad324 VP peak is about 4-fold larger than that under the Ad336 peak.
Figure 3B:
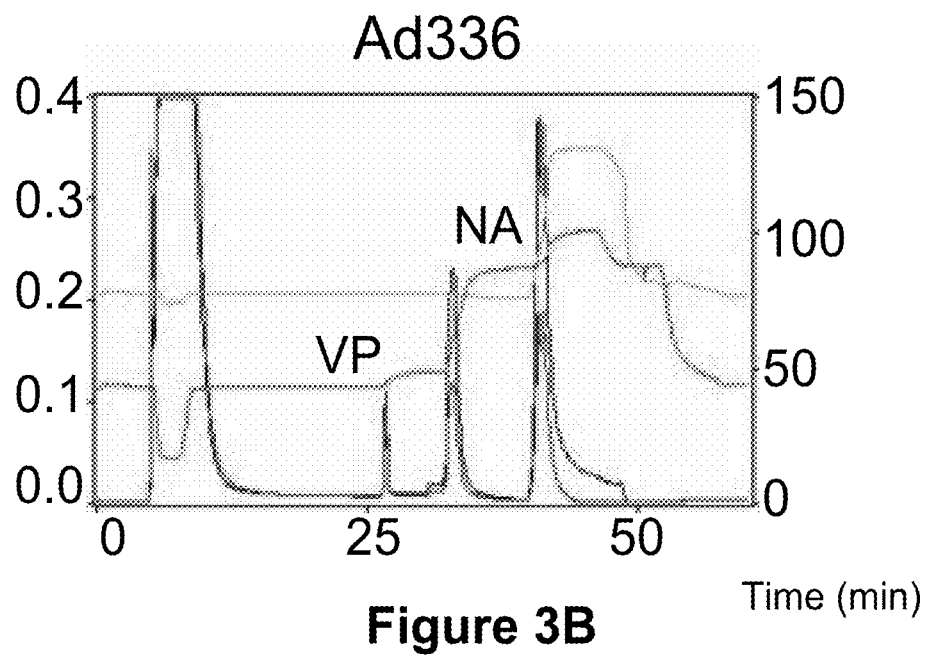

Monolayers of 293 cells were infected with equivalent amounts of Ad324 or Ad336 infectious particles. Medium and cells were harvested 2 days after the infection, frozen/thawed once, and centrifuged for 1 minute at 311 g. The supernatant was 0.45 µm filtered and applied on a 1.0 ml HiTrap column equilibrated with 0.425 M NaCl-20 mM Tris, pH 7.5. Virus was eluted with a step gradient to 0.5 M NaCl and nucleic acids (NA) were eluted with another step gradient to 1 M NaCl. The area under the Ad324 VP peak is about 4-fold larger than that under the Ad336 peak (FIGS. 3A and 3B).

Without being limited by theory, it is essential to have a helper virus that yields high virus amounts for TP-ITR production, since the virus amplification in bioreactors represents a significant part of the bioprocess costs. A helper virus that replicates better is also likely to generate higher amounts of gutless virus particles.

Example 3

Virus Amplification

This example describes virus amplification.

3.1. Comparison of growth of 293 cells in different serum-free suspension media

Several commercially available serum-free suspension culture media were screened for adenovirus production: GT3 medium (Sigma), CD293 medium (Invitrogen), SFM4HEK293 and CDM4 (Hyclone), and a 50-50 blend GT3:DMEM supplemented with 5% cosmic calf serum. The 293 cells were adapted in suspension culture in each of these media. Growth curves were established, and adenovirus yields were determined under the same conditions of infection. These studies were performed using 125- and 250-mL shaker flasks, with working volumes of 20 and 40 mL, respectively. Virus infections were performed using virus Ad324 and determination of virus yields were performed by analytical HPLC using the method described in section 2.9.

For cell growth to high densities, CDM4 medium (Hyclone) was selected among the other media for the following advantages: a) high cell densities achievable in batch mode (up to $6.3 \times 10^6$ cells/mL); b) high cell densities achievable in perfusion mode (up to $1.2 \times 10^7$ cells/mL); c) doubling time for 293 cells is about 30 hours (comparable to those obtained with GT3 or CD293 media); d) cells do not form large clusters, they are healthier and can be counted with more precision; e) competitive price; f) available in powder or 20-L bags; and g) good technical support.

For virus production, an iron-free version of the SFM4HEK293 medium (Hyclone) was chosen for the following advantages: a) it can support cell growth for up to 2 passages, and is therefore suitable for virus infection (2-3 days); b) it provides a cleaner chromatography profile than the SFM4 medium supplemented with iron; c) it is not more expensive than the original iron-containing medium; d) it produces high yields of virus particles (approximately 40,000 VP/cell); e) it is less expensive; f) available in powder or 20-L bags; and g) good technical support.

3.2. Scaling up 293 cell suspension culture in fed-batch and under perfusion

Figure 5:
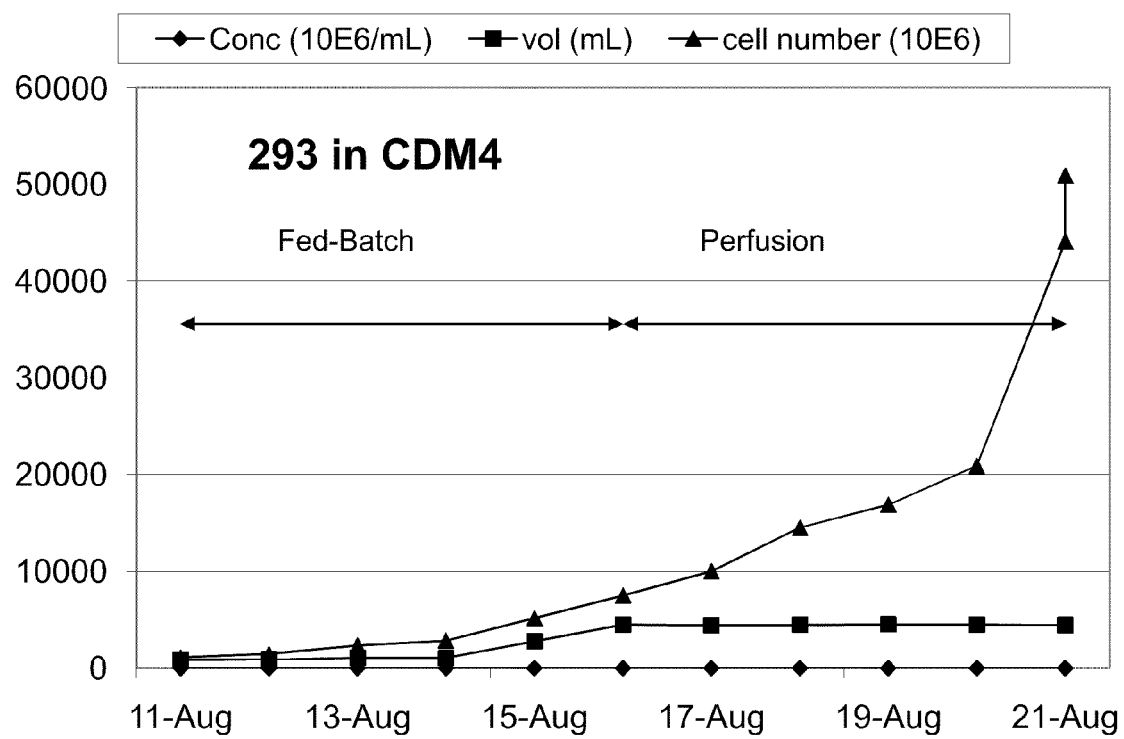
FIG. 5 shows the scale-up of a 293 cell suspension culture in CDM4 under perfusion using a WaveBiotech bioreactor.

Bioreactors were used to scale up the 293 cell suspensions. A WaveBiotech bioreactor System 2/10 EH was used to grow 293 cells under perfusion at densities as high as $1.2 \times 10^7$ cells/ml (5 L volume). The cells grown under these conditions provided the same virus yields as those obtained with shaker flasks, confirming the scalability of the system. FIG. 5 shows the scale-up of a 293 cell suspension culture in CDM4 under perfusion using a WaveBiotech bioreactor. 293 cells were inoculated in 300 mL medium at a density of $1 \times 10^6$ cells/mL. Fresh medium was added each time the density reached $2 \times 10^6$ cells/mL. After the total volume reached 4.5 L, perfusion was started until the density was over $8 \times 10^6$ cells/mL. At that time, the cell density was adjusted to $10^7$ cells/mL and 2.5 L cell suspension was transferred to another Cellbag 10L for virus infection. Infected cells were transferred again to a CellBag 50L containing 22.5 L SFM4HEK medium (without iron). Virus production proceeded for 2-3 days before harvest.

3.3. Virus infection and harvest 3.3.1. VP/cell ratio for infection 293 cells suspensions were prepared in 250 ml flasks (volume: 40-60 ml). Virus yields obtained after infecting 293 cells cultured in various media with different virus doses were compared. The doses corresponded to approximately 30 (1.5 infectious units (IU)/cell), 60 (3 IU/cell), and 120 (6 IU/cell) VP/cell. Virus yields were estimated by analytical HPLC using a 1 ml Q-Sepharose XL HiTrap column. Infection of 293 cells with 60 VP/cell was sufficient to gain maximal virus yield.

3.3.2. Cell density at time of infection

Cells were infected at densities $1 \times 10^6$, $5 \times 10^6$, and $10 \times 10^6$ cells/ml with adenovirus at a ratio of 60 VP/cell. Cells were left in contact with the virus with slow shaking, fast enough to maintain a homogenous cell suspension. After 1.5 hours, medium was added to obtain a cell density of $1 \times 10^6$ cells/ml and cells were cultured under normal shaking conditions for 2 days. Virus yields were determined by analytical HPLC, using Q-Sepharose XL HiTrap columns (1 ml). No significant difference in viral yield between the conditions was observed.

3.3.3. Cell density during virus production

The effect of cell density on virus yield during the phase of virus production was determined. Virus yield obtained from cultures grown at densities of $1.0 \times 10^6$, $1.5 \times 10^6$ and $2.0 \times 10^6$ cells/ml. The highest yields were obtained when cells are cultured at $1 \times 10^6$ cells/ml density, but yield drops only 10% at higher cell densities ($1.5 \times 10^6$ and $2 \times 10^6$ cells/ml). These results are surprising and unexpected, as previous reports of a 'cell density' effect set an upper limit for cell density to $1 \times 10^6$ cells/ml beyond which the virus yield drops strongly.

3.3.4. Time for harvesting infected cells

The optimal time to harvest infected cells was determined by infecting 293 cells grown in various serum-free culture media with a 60 VP/cell dose, harvesting aliquots of the culture at days 2, 3 and 4 post-infection, and determining virus production by analytical HPLC, using Q Sepharose XL 1 mL Hitrap columns. Results show that the optimal time for virus harvest is 2 to 3 days after the infection. A 20% decrease in virus yield is observed at day 4 with most media.

3.3.5. Cell lysis by freeze-thaw (small scale)

Freeze-Thaw was used to lyze small batches of infected cells. Freeze-thaw (F/T) can easily and quickly be performed in tubes (up to 50 mL) or bags (0.5-5 L). In the latter case, bags are laid flat on a metallic shelf of a $-70°$ C. freezer. One-liter infected cell lysate can be frozen in about 30 min and can be thawed in less than 5 min.

3.3.6. cell lysis by freeze-thaw (large scale)

Infected cells were lyzed with a detergent, without denaturing the virus. Triton X-100 (0.1%) in the presence or absence of 0.05% polysorbate-80 was used. Cell lysis in these conditions was as good as freeze-thaw, and 0.1% Triton X-100 alone was sufficient. The detergent is added directly to the Cellbag 50L, after the temperature of the medium has come down to room temperature.

3.3.7. cell lysate clarification

Lyzed cell extract was clarified by centrifugation (3600 g, 20 min). The supernatant was then filtered through a train of filters including (from inlet to outlet): Millipore AP25/AP15, RW19/1.2 µm, and RW6/0.45 µm. The filtrate was collected into a sterile container. NaCl was added to 0.425 M. The filtrate was then loaded on an anion-exchange chromatography column as described in Example 4.

Example 4

Virus Purification by Chromatography

This example describes virus purification by chromatography.

4.1 Analytical chromatography method for rapid virus quantification

Virus yields were determined with an analytical chromatography method based on anion exchange that provided the best separation of virus particles from the media and cell lysate components, in particular nucleic acids. QSXL gave the best resolution between VP and DNA, while Fractogel produced the best separation between VP and media components. In some cases the virus peak obtained on Fractogel would overlap with a peak containing small undesirable DNA fragments. Therefore QSXL resin was used.

Figure 6:
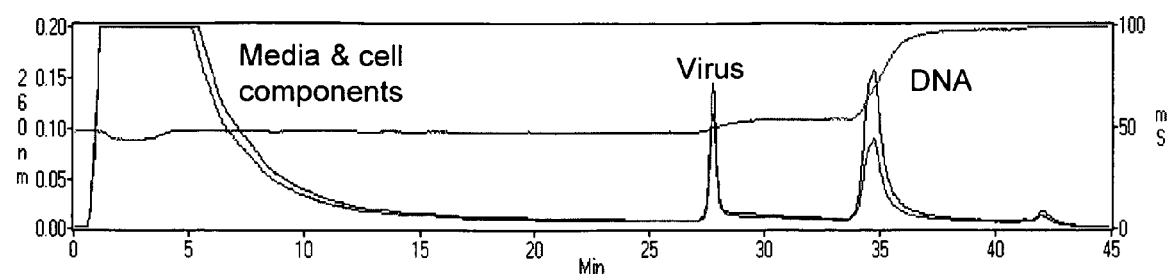
FIG. 6 shows the separation of virus particles from the SFM4HEK293 medium components and nucleic acids (DNA & RNA). The conductivity of a 3.5 mL sample of infected cell lysate obtained from the bioreactor was adjusted to the equivalent of 0.425 M NaCl. The sample was loaded on a QSXL Hitrap column (1 ml). Virus was eluted at a 0.5 M NaCl step gradient. Nucleic acids were eluted by raising the NaCl concentration to 1 M.

FIG. 6 shows the method developed for QSXL gives a linear response with virus loads ranging from $10^9$ to $10^{11}$ VP. Spiking experiments were also performed with infected cell lysate and confirmed the quantitative nature of the method.

4.2 Scalable chromatography system for adenovirus purification

Figure 7:
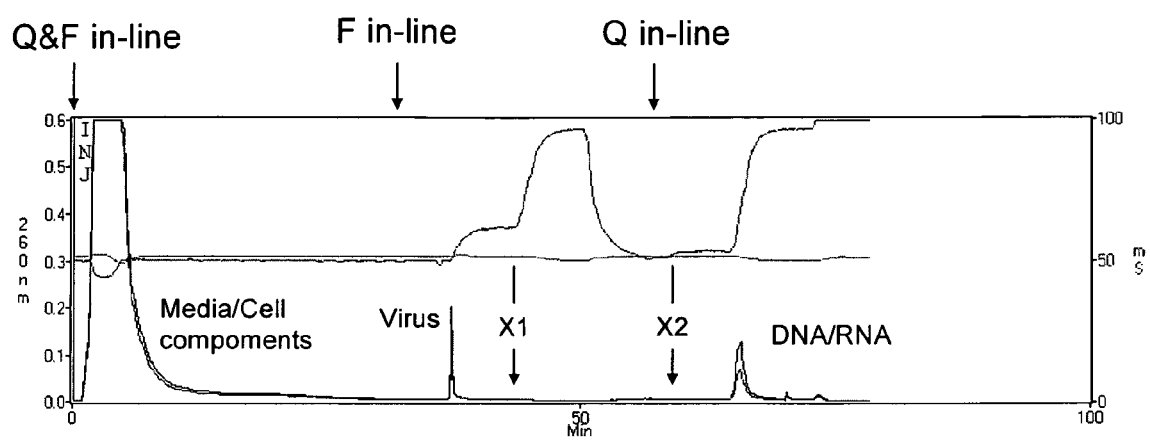
FIG. 7 shows separation of virus particles from media and cell components and nucleic acids using a tandem QSXL-DEAE Fractogel system. Filtered infected cell lysate (4 mL) were loaded onto the system. Note the absence of nucleic acids eluting from the F column when the [NaCl] is raised to 1 M (point marked X1), and the absence of detectable virus eluting from the Q column when the [NaCl] is raised to 0.5 M (point marked X2). Blue line: Abs260; red line: Abs280; green line: pH; pink line: conductivity.
Figure 8:
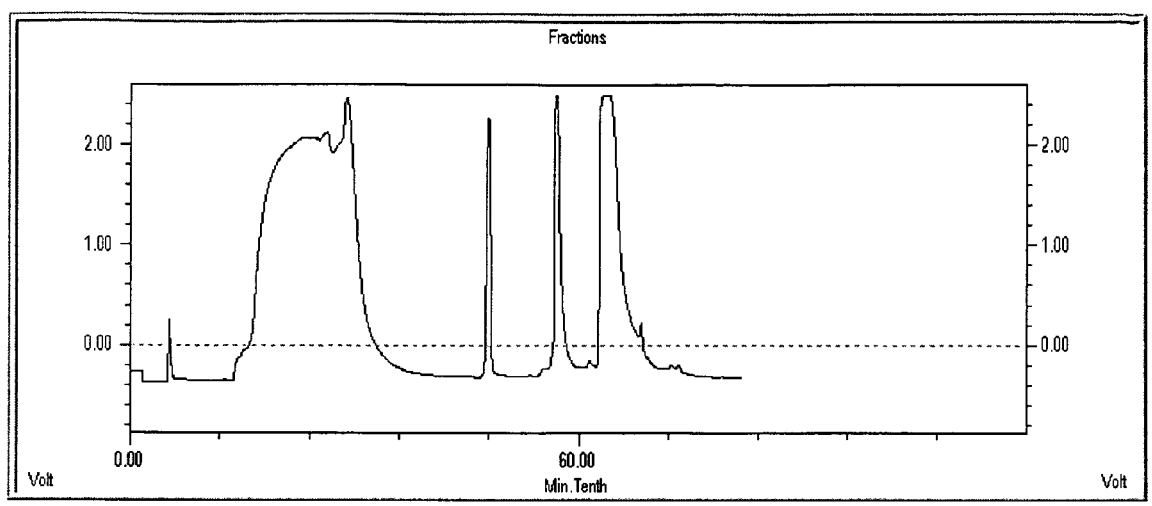
FIG. 8 shows large-scale adenovirus purification. Clarified infected cell lysate (25 L) was adjusted to 0.425 M NaCl and loaded on a 4-L column packed with QSXL resin. After column wash, virus (VP) was eluted with 0.5 M NaCl. DNA was eluted with 1 M NaCl. Typically the virus was recovered in 2 L, concentrated to approximately 100 mL, then buffer-exchanged by diafiltration.

Saturation experiments of a 1-mL QSXL column with infected cell lysate indicated that the capacity of QSXL resin for adenovirus particles would not exceed 8 mL cell lysate/ml resin. In order to increase the capacity of the resin for VP, nucleic acids (DNA and RNA) present in the cell lysate were removed. To avoid the use of the endonuclease benzonase (which can generate small DNA fragments that co-elute with the virus and must be inactivated completely before we purify the TP-DNA from the virus particles), a QSXL/DEAE Fractogel tandem-column system where QSXL acts as a trap to capture exclusively the nucleic acids, and where Fractogel capture the virus particles, was utilized. In this system, the filtered cell lysate is adjusted to a defined conductivity value with NaCl, and is loaded to the system. After impurities are washed away, the QSXL column is disconnected from the system, and virus is eluted from the Fractogel column by raising [NaCl] to 0.6 M (FIG. 7).

The virus peak obtained from the Fractogel column was collected. No nucleic acid beside the viral DNA was detected on EtBr-stained agarose gel The capacity of the system by saturating 1-mL tandem columns with infected cell lysate was determined. Data suggests that the 1-mL QSXL column can sufficiently bind DNA in at least 150 ml ICL to prevent its cross-over onto the F column, and that 50 ml infected cell lysate is about the maximal volume to load on a 1 ml HiTrap F column to bind VP efficiently.

4.3 Adenovirus purification scale-up

Adenovirus purification was scaled-up on a QSXL resin due to its high capacity for adenovirus and nucleic acids and good separating power between these two components. A step-gradient method that gives a good separation between adenovirus and nucleic acids peaks, and that can be adapted easily to a large-scale low-pressure purification system was used. Using a 1-mL Hitrap QSXL column, the virus recovery from crude infected cell lysate remains quantitative for up to 12-mL loads. Therefore a 4-L column was packed with that resin in order to be able to purify virus from a 25-L cell lysate obtained from the bioreactor. In the developed procedure, the clarified infected cell lysate is adjusted to 0.425 M NaCl by addition of a concentrated NaCl solution. This prevents many components from binding to the column during loading. After the cell lysate is loaded and the column washed, the virus is eluted with 0.5 M NaCl. The virus peak (up to 2 L) is concentrated to 100 mL using a Pellicon XL Biomax 300 kDa cassette mounted on a Labscale TFF system, and then buffer-exchanged by diafiltration using GTS buffer (2.5% glycerol, 25 mM NaCl, 20 mM Tris-HCl pH 8.0). Typically, $1.2 \times 10^{15}$ VP from 25 L infected cell lysate was recovered.

Example 5

Viral TP-DNA Purification

This example describes viral TP-DNA purification.

The purification of the TP-ITR complex involves isolating the terminal protein-bound viral DNA from the viral capsid proteins. This step was performed by size exclusion chromatography.

Figure 9:
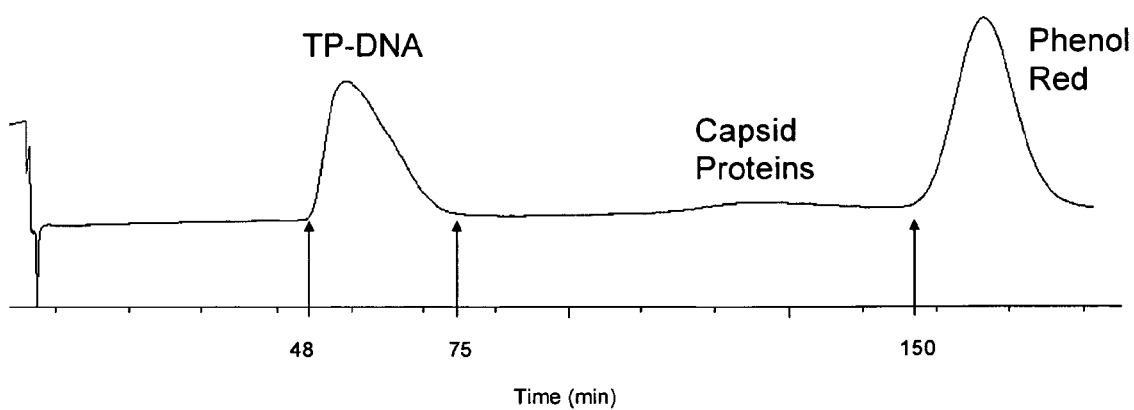
FIG. 9 shows large-scale purification of viral TP-DNA by size-exclusion chromatography. $2.5 \times 10^{14}$ VP were denatured in 150 mL GnHCl 4 M, then loaded on a 5-L column packed with a 32 cm-high bed of Sepharose 4FF. The TP-DNA peak (approximately 800 mL) was collected and dialyzed against 10 mM Tris, pH 7.5, 10 L changes using 2 Spectra/Por #132726 MWCO 3500 membranes.

Sepharose 4FF (GE Healthcare) resin was used. A 160-mL 30-cm bed height column was packed and several runs were performed with increasing amounts of virus. Up to 16 mL virus suspension containing $3.2 \times 10^{13}$ virus particles (i.e. 10% total column volume) could be loaded on the column. FIG. 9 shows achievement of a good separation (12 min interval) between TP-DNA and viral capsid proteins.

Viral TP-DNA was collected, concentrated using a centrifugal device, and quantified. Yield of TP-DNA after the concentration step was about 65% of the amount loaded on the chromatography column.

Quality control assays were performed, including: detection of residual chromosomal DNA from 293 cells by quantitative slot blot analysis, detection of residual adenovirus capsid proteins by western blot using a polyclonal anti-Ad5 antibody (Novus Biologicals, Littleton, Colo. #NB600-403), detection of infectious adenovirus particles (infection of 293 cell monolayers and cultures up to 3 weeks), and endotoxin detection.

The purification of viral TP-DNA was scaled-up on a 5-L column packed with a 32 cm-high bed of Sepharose 4FF. Virus particles are denatured by adding 1 volume of GnHCl 8 M. Up to 300 mL of the mixture is loaded on the column equilibrated with 2 M GnHCl. The TP-DNA peak is collected and dialyzed immediately against 10 mM Tris pH 7.5. Concentration of the peak is avoided, since it promotes irreversible TP-DNA aggregation.

Example 6

TP-ITR Purification

Separation of the TP-ITR complex from a series of DNA restriction fragments (ranging from 5 to 13 kb) is performed. These restriction fragments are obtained by digesting the TP-DNA with DraIII or BstXI, which generate non-palindromic sticky ends on the TP-ITR complex. This purification is achieved in 2 steps, first by Hydrophobic Interaction chromatography (HIC), then on an anion-exchange column (AIEX).
6.1 Hydrophobic Interaction Chromatography (HIC)

Figure 10:
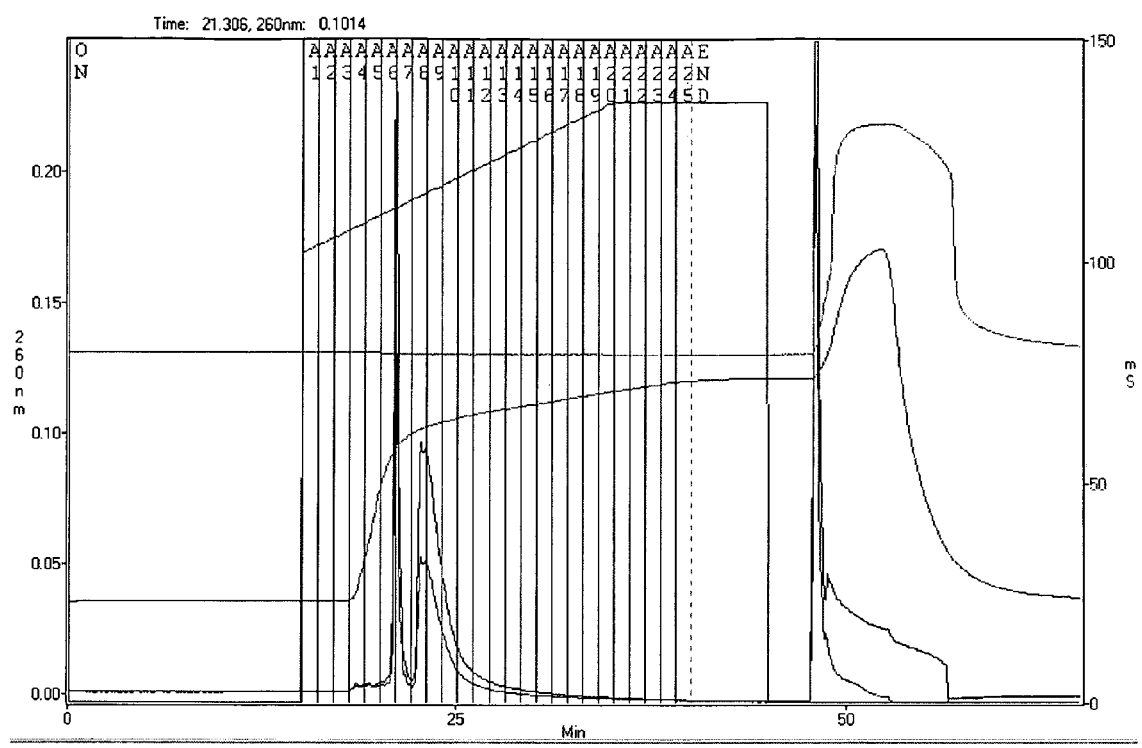
FIG. 10 shows purification of the TP-ITR on Resource Q column. The TP-ITR complex was separated from larger DNA fragments that co-eluted from the HIC column.

The DraIII digestion mixture of the TP-DNA, containing the TP-ITR complex of interest and a series of DNA fragments ranging from 5 to 13 kb is first adjusted to 1 M $AmSO_4$ by the addition of $\frac{1}{3}$ Vol 4 M $AmSO_4$, at 25° C. The sample is then loaded on a 16 mm-diameter 5-mL Phenyl-HP column equilibrated with 20 mM sodium phosphate monobasic+30 mM sodium phosphate dibasic+1 M $AmSO_4$, pH 7.0, at a flow rate of 2 mL/min, using a syringe pump working in continuous mode. During loading, the TP-ITR complex as well as other TP-DNA fragments, which could be products of incomplete digestion with DraIII, binds onto the column. The DraIII or BstXI fragments that do not carry the TP flow through the column and are discarded. The TP-ITR is eluted from the column using a salt-free buffer (20 mM sodium phosphate monobasic+30 mM sodium phosphate dibasic, pH 7.0).
6.2 Anion-exchange chromatography The TP-ITR complex is further purified by anion-exchange chromatography. This step provides for removal of the DNA fragments that co-eluted with the TP-ITR complex from the phenyl-HP column. These contaminating DNA fragments are larger than the ITR, and could originate from TP-DNA being incompletely digested with the restriction enzyme. HIC fractions containing the TP-ITR are pooled and loaded directly on a 1-mL Resource Q column (Amersham #17-117-01) equilibrated in 20 mM Tris-HCl+0.2 M NaCl, pH 7.5. A gradient from 700 mM to 800 mM NaCl over 10 min is run through the column. FIG. 10 shows the TP-ITR eluted as a single peak separated from the larger DNA fragments.
6.3 Quality Control Quality control experiments are performed including: identification of the TP-ITR on PAGE; detection of helper viral DNA by agarose gel electrophoresis and EtBr staining, quantitative slot blot analysis with an Ad5-specific probe and chemiluminescent detection, and by real-time quantitative PCR; detection of viral proteins by western blot, using an anti-Ad5 polyclonal antibody; detection of infectious adenoviral particles; detection of infectious genomes; detection of gram-negative bacterial endotoxin; ligation efficiency; virus recovery efficiency; sterility and stability.

Example 7

TP-ITR Method for the Production of Gutless Adenovirus Vectors

Figure 11:
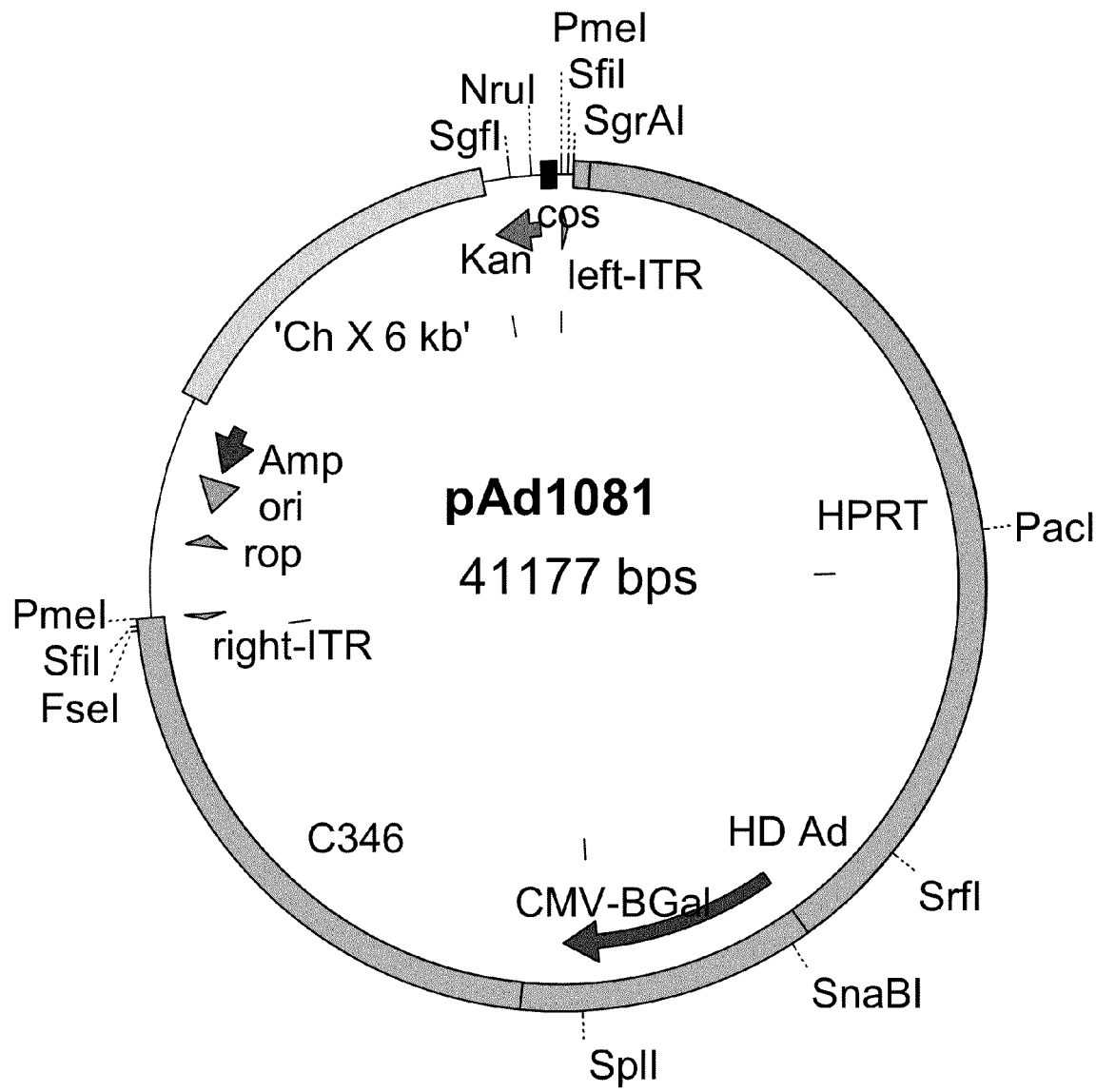
FIG. 11 shows the map of pAd1081. The plasmid contains the sequence of a gutless adenovirus vector (green bar) between 2 PmeI restriction sites. pAd1081 contains a β-galactosidase-expressing cassette, and sequences from the HPTR locus and cosmid C346 as stuffer. SfiI sites have been inserted between the left ITR and HPRT sequence, and between the right ITR and C346 sequence. SfiI-digested pAd1081 can be linked to the TP-ITR complex via a simple and efficient DNA ligation reaction.

This example describes the TP-ITR method for constructing gutless adenovirus vectors.
7.1 Constructing gutless plasmids adapted to the TP-ITR method A plasmid containing the sequence of a gutless adenovirus genome flanked by SfiI sites was constructed (pAd1081, FIG. 11). That plasmid is based on pGS46 and contains the first 440 bp from wild-type Ad5 genome, including the left ITR and packaging signal, a 16 kb-long stuffer DNA sequence from the HPRT locus, a cassette expressing β-galactosidase under the control of a CMV promoter and SV40 poly-adenylation signal, a 9 kb-long stuffer DNA sequence from cosmid C346, and the right ITR (corresponding to sequence nt 35818 to 35935 in Ad5 genome). Two SfiI sites were inserted into the gutless genome: one between the left ITR and the packaging signal, and a second between the right ITR and cosmid C346 sequence. These SfiI sites generate sticky ends that are complementary with those presents on the TP-ITR complex.
7.2 Constructing a helper virus genome deficient for packaging The conventional method for generating HD adenoviruses uses a helper virus in which the packaging signal is flanked by FRT or Lox recombination sites, and is excised from the viral genome in cells expressing the FLPe or Cre recombinases, respectively. This system has the disadvantage that the HD virus preparation may contain a small percentage of helper virus because the recombinase-mediated excision of the packaging signal is not 100% efficient.

In the TP-ITR method for generating HD viruses (FIG. 4), the helper virus is the virus from which the TP-ITR was purified. In addition, the first step of the process, i.e. the co-transfection of the gutless plasmid and helper plasmid into 293 cells allows us to use a variant of the helper plasmid, from which the packaging signal has been deleted. In that way, a virtually helper-free cell population may be obtained upon the transfection step (passage "0").

pAd337, a cosmid containing the entire sequence of virus Ad324, was constructed. The packaging signal was deleted by excising the 167-bp SgrAI-BglII fragment from pAd1052, a shuttle vector containing the left end of the adenovirus genome. The pAd1052 derivative was combined with pAd324 to construct pAd337. pAd337 was amplified and purified on CsCl gradient. After digestion with either SfiI or PmeI, the large 32 kb fragments were separated from the 10-kb backbone fragments on 5-10% NaCl gradients.

Figure 12:
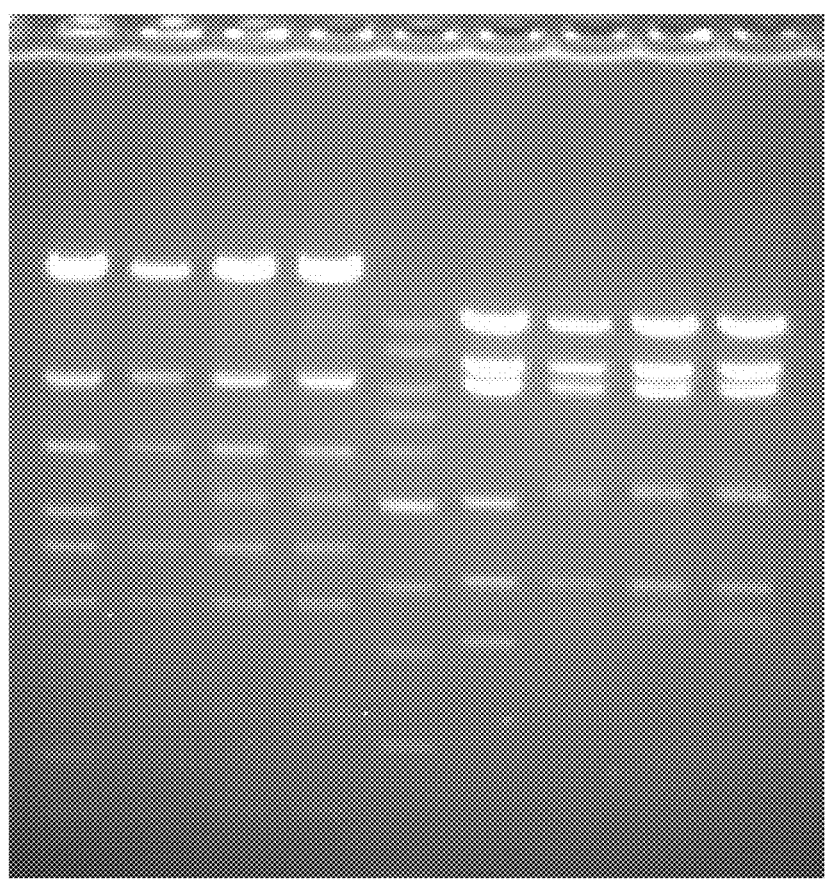
FIG. 12 shows the assessment of the efficiency of ligation of the TP-ITR to the SfiI-digested gutless and helper plasmids. Various amounts of TP-ITR (0, 8, 16, and 32 μL of the preparation obtained in Example 7) were ligated with 2 μg pAd1081 or pAd337 that had been digested with SfiI and purified on NaCl gradient. After 3 hours at room temperature (approximately 25° C.), the ligase was heat inactivated. Aliquots of the various reactions were digested with AflIII or XhoI and run on an agarose gel. The green arrows indicate the AflII and XhoI terminal fragments from SfiI-digested pAd337 and pAd1081, respectively. The red arrows highlight the shift that these terminal fragments undergo upon ligation with the TP-ITR. Expected fragments: pAd337/SfiI+AflII=17355+6029+3891+2724+2296+1661+914+701+203 pAd1081/SfiI+XhoI=10104+7208+6203+2050+2999+1586

7.3 Comparison of the efficiency of gutless virus recovery with or without TP-ITR 7.3.1 Ligating the TP-ITR to the gutless and helper plasmids SfiI-digested pAd1081 and pAd337 were ligated to the TP-ITR complex obtained by purification on a tandem HIC-Resource Q, as described in Example 6. The ligation was performed using a T4 DNA ligase (NEB #M0202), for 3 hours at room temperature. In order to assess the efficiency of the ligation reaction, the ligated DNAs were digested with AflII (for pAd337/SfiI) or XhoI (for pAd1081/SfiI). FIG. 12 shows that the ligation of the TP-ITR to the terminal AflII fragments from pAd337/SfiI (2724 bp and 914 bp) and the terminal XhoI fragments from pAd1081/SfiI (1586 bp and 2999 bp) induces a shift of these bands towards higher molecular weights on an agarose gel. When larger amounts of TP-ITR are used in the ligation reaction (i.e. 16 or 32 μL), no band corresponding to the terminal fragments devoid of TP-ITR is visible on gel, indicating that the reactions are performed to almost completion.

A vial of 293 cells in DMEM/10% FBS was seeded into a culture dish. Medium was changed after 2 days. The cells (~100% confluent) were then split to separate dishes such that a 60% and a 30% confluence were subsequently expected.

7.3.2 Rescuing gutless virus from gutless and helper plasmids

The gutless and helper DNAs ligated to the TP-ITR were transfected into 293 cells using the calcium-phosphate precipitation method. The cells split at 60% (which were approximately 80% confluent) were transfected with a mixture of pAd337/SfiI and pAd1081/SfiI with or without TP-ITR for 1.5 hours, then DMEM was added, and the culture incubated at 37° C. overnight. Two days after the transfection, cells and medium were harvested and frozen. The virus particles were released from the cells by one freeze-thaw cycle. In order to quantify the titer of gutless virus, the crude viral extracts obtained were used to infect new monolayers of 293 cells. After 24 hours these cells were stained for β-galactosidase expression. The results are summarized in Table 1. They show that the titer of gutless virus obtained using the TP-ITR is at least a 3 orders of magnitude higher than the titer obtained using the same vectors lacking the TP-ITR.

TABLE 1

Rescue of gutless adenovirus from plasmid DNA using the TP-ITR method.

|  | +TP-ITR | | | No TP-ITR | |
| --- | --- | --- | --- | --- | --- |
|  | (32 U) | (16 U) | (8 U) | | |
| Helper plasmid (pAd337) | 2 μg | 2 μg | 2 μg | 2 μg | 4 μg |
| Gutless plasmid (pAd1081) | 2 μg | 2 μg | 2 μg | 2 μg | 4 μg |
| Blue forming units (BFU) | $1.0\,10^8$ | $1.3\,10^8$ | $7.3\,10^7$ | $4.3\,10^4$ | $5.9\,10^4$ |
| Enhancement by TP-ITR | 2356 | 3012 | 1680 | 1 | 1.4 |

Example 8

Characterizing the Gutless Virus Obtained Using the TP-ITR Method: Titer, Genome Integrity, Presence of Helper Virus, and Presence of RCA The crude viral extract obtained in Example 8 was used to infect monolayers of 293-FLPe cells with the helper virus Ad336. Cells and medium were harvested two days after the infection, and frozen/thawed twice in order to release the virus particles from the cells. This amplification was repeated several times, each time increasing the number of cells being infected. At the end of the last cycle, the virus particles were purified on CsCl gradients.

The identity of the gutless virus was verified by extracting the DNA from virus particles by proteinase K digestion. The viral DNA was digested by a series of restriction enzymes. The restriction patterns were confirmed by agarose gel electrophoresis.

The titer of the gutless virus, and the presence of helper and replication-competent (RCA) virus particles in the gutless virus preparation were assessed by multiplex real-time PCR using an assay developed by Puntel et al. (Quantification of High-Capacity Helper-Dependent Adenoviral Vector Genomes In Vitro and In Vivo, Using Quantitative TaqMan Real-Time Polymerase Chain Reaction. *Hum Gene Ther*. May 2006; 17(5): 531-544.), incorporated herein by reference in its entirety). In that assay, sequences specific for each virus type are amplified using pairs of primers linked to different fluorophores. For the gutless virus genome, the primers amplify a region of the β-galactosidase coding sequence. For the helper virus, the L3 region of the adenovirus genome is amplified. For RCA, a segment of the E1 region is amplified.

The biological titer of the gutless virus particles was also assessed by infecting reporter cells and staining for β-galactosidase expression. The titer of helper virus was also assessed by infecting 293 cells with the gutless virus suspension and monitoring for plaque formation. The titer of RCA in the gutless virus preparation was also assessed by infecting Hela cells with the gutless virus suspension and monitoring for plaque formation.

The invention claimed is:
1. A method of making a recombinant adenovirus vector, the method comprising the steps:
    (a) insertion of one or a group of endonuclease recognition sites into the genome of a helper adenovirus immediately downstream from adenovirus inverted terminal repeats;

(b) amplification of the helper adenovirus, wherein the helper adenovirus contains adenovirus terminal protein bound to adenoviral DNA, wherein the adenoviral DNA is an inverted terminal repeat DNA sequence, wherein the adenovirus terminal protein bound to the inverted terminal repeat DNA sequence forms an adenovirus terminal protein-inverted terminal repeat DNA sequence complex;

(c) purification of the adenovirus terminal protein-inverted terminal repeat DNA sequence complex from the helper adenovirus; and, (d) in vitro DNA ligation of the inverted terminal repeat DNA sequence of the adenovirus terminal protein-inverted terminal repeat DNA sequence complex to heterologous linear nucleic acid sequence by purified DNA ligase, wherein the heterologous linear nucleic acid sequence contains an adenovirus packaging signal, and wherein the adenovirus terminal protein-inverted terminal repeat DNA sequence complex ligated to said heterologous linear nucleic acid sequence is used to make recombinant adenovirus vector.

2. The method according to claim 1, wherein the endonuclease sites produce non-palindromic sticky ends upon cleavage.

3. The method according to claim 1, wherein the helper adenovirus is a helper adenovirus used to make gutless adenovirus vectors.

4. The method according to claim 1, wherein the inverted terminal repeat DNA sequence is about 50 base pairs to about 170 base pairs.

5. The method according to claim 4, wherein the inverted terminal repeat DNA sequence is terminated with the terminal protein on one end of the inverted terminal repeat DNA sequence and with a non-palindromic sticky end on the other end of the inverted terminal repeat DNA sequence.

6. The method according to claim 1, wherein adenovirus terminal protein-inverted terminal repeat DNA sequence complex is purified from cells containing replicating helper adenovirus.

7. The method according to claim 1, wherein the heterologous linear nucleic acid sequence is DNA used to make adenovirus vectors.

8. The method according to claim 1, wherein the recombinant adenovirus vector is a gutless vector devoid of all viral sequences except those required for replication and packaging.

9. The method according to claim 1, wherein the heterologous linear nucleic acid sequence is terminated with a non-palindromic sticky end.

10. A recombinant adenovirus from which the adenovirus terminal protein can be purified, which comprises:
   a) an inverted terminal repeat DNA sequence;
   b) at least one endonuclease site, wherein the endonuclease site is capable of producing identical, non-palindromic sticky ends adjacent to inverted terminal repeat DNA sequences;
   c) a packaging signal;
   d) a pair of Lox sites or a pair of Frt sites flanking the packaging signal;
   e) a deletion in the E1 region; and
   f) a stuffer DNA fragment in the E3 or E4 region;
wherein the stuffer fragment increases the size of the viral genome to about 36 kilobases,
wherein the recombinant adenovirus is a helper-independent adenovirus,
and wherein the helper-independent virus can be deleted for at least one viral gene.

11. The recombinant adenovirus according to claim 10, wherein the endonuclease site is DraIII restriction enzyme site or a SfiI restriction enzyme site.

12. The recombinant adenovirus according to claim 11, wherein one or more of the DraIII restriction enzyme sites that are present naturally in the adenovirus genome have been mutated.

13. The recombinant adenovirus according to claim 10, wherein the endonuclease site is a BstXI restriction enzyme site or an I-SceI enzyme site.

14. The recombinant adenovirus according to claim 13, wherein one or more of the BstXI restriction enzyme sites that are present naturally in the adenovirus genome have been mutated.

15. The recombinant adenovirus according to claim 10, wherein the packaging signal has minimal homology to the packaging signal of a gutless plasmid.

16. The recombinant adenovirus according to claim 10, wherein the stuffer DNA does not encode for a protein or a regulatory sequence.

17. The recombinant adenovirus according to claim 10, wherein the stuffer DNA does not share homology with the chromosomes of the cell where the virus is propagated, the chromosomes of the cell to which it is targeted, or the gutless virus genome.

* * * * *